(12) United States Patent
Kerins et al.

(10) Patent No.: US 10,957,221 B2
(45) Date of Patent: Mar. 23, 2021

(54) PHYSIOLOGICAL PHANTOMS INCORPORATING FEEDBACK SENSORS AND SENSING MATERIALS

(71) Applicant: SYNAPTIVE MEDICAL INC., Toronto (CA)

(72) Inventors: Fergal Kerins, Toronto (CA); Arun Victor Jagga, Toronto (CA); Siu Wai Jacky Mak, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 517 days.

(21) Appl. No.: 15/546,916

(22) PCT Filed: Jan. 29, 2015

(86) PCT No.: PCT/CA2015/050065
§ 371 (c)(1),
(2) Date: Jul. 27, 2017

(87) PCT Pub. No.: WO2016/119039
PCT Pub. Date: Aug. 4, 2016

(65) Prior Publication Data
US 2018/0033339 A1 Feb. 1, 2018

(51) Int. Cl.
*G09B 23/30* (2006.01)
*H04B 10/071* (2013.01)
(Continued)

(52) U.S. Cl.
CPC ............... *G09B 23/30* (2013.01); *G01L 1/00* (2013.01); *G01L 1/246* (2013.01);
(Continued)

(58) Field of Classification Search
None
See application file for complete search history.

(56) References Cited

U.S. PATENT DOCUMENTS

2007/0021738 A1* 1/2007 Hasser ................. A61B 90/361 606/1
2010/0056904 A1* 3/2010 Saunders ................ A61B 6/12 600/424
(Continued)

OTHER PUBLICATIONS

International Search Report from PCT/CA2015/050065 dated Nov. 6, 2015.
(Continued)

*Primary Examiner* — James B Hull

(57) ABSTRACT

Disclosed herein are physiological phantoms incorporating sensors and sensor materials integrated with a tissue phantom of an anatomical part. The sensors and sensor materials include small diameter optical fibers containing Bragg gratings, thermochromic materials, electrical strain gauges, flexible strain gauges, shape sensing cables, electrochromic materials and etc. The sensors and sensing materials may mimic tissue as part of the tissue phantom. They may mimic the directionality, density, elasticity of the anatomical tissues they may be mimicking. The sensors and sensing materials may be sensitive to strain, heat, electricity, shape, light, and etc. similar to what may occur during medical procedures using various medical devices and tools such as a scalpel, a needle, a deep brain stimulation probe, a port used in brain or spinal surgery and etc.

16 Claims, 27 Drawing Sheets

(51) Int. Cl.
*G09B 23/28* (2006.01)
*G09B 23/32* (2006.01)
*G09B 23/34* (2006.01)
*G01L 1/00* (2006.01)
*G01L 1/24* (2006.01)
*G01M 11/08* (2006.01)
*A61B 17/00* (2006.01)

(52) U.S. Cl.
CPC ......... *G01M 11/086* (2013.01); *G09B 23/285* (2013.01); *G09B 23/286* (2013.01); *G09B 23/32* (2013.01); *G09B 23/34* (2013.01); *H04B 10/071* (2013.01); *A61B 2017/00716* (2013.01)

(56) References Cited

U.S. PATENT DOCUMENTS

| | | | | |
|---|---|---|---|---|
| 2010/0099066 A1* | 4/2010 | Mire | ...................... | G09B 23/34 434/272 |
| 2013/0157240 A1* | 6/2013 | Hart | ...................... | G09B 23/30 434/267 |

OTHER PUBLICATIONS

International Written Opinion Report from PCT/CA2015/050065 dated Oct. 28, 2015.

\* cited by examiner

[Cooper, David J. F. Time Division Multiplexing of a Serial Fibre Optic Bragg Grating Sensor Array. Ottawa: National Library of Canada, 1999. Print.]

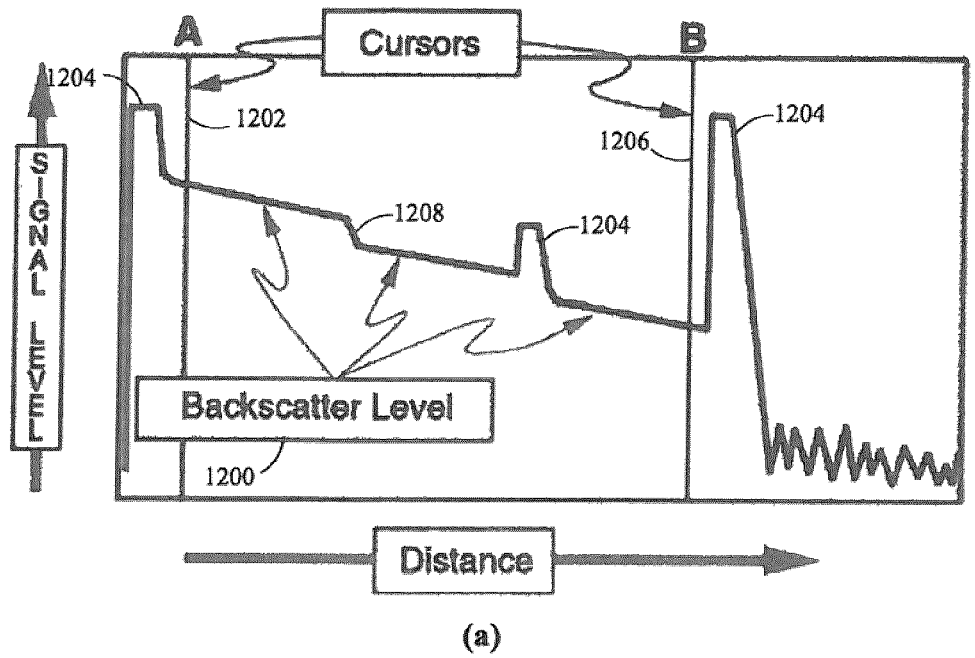
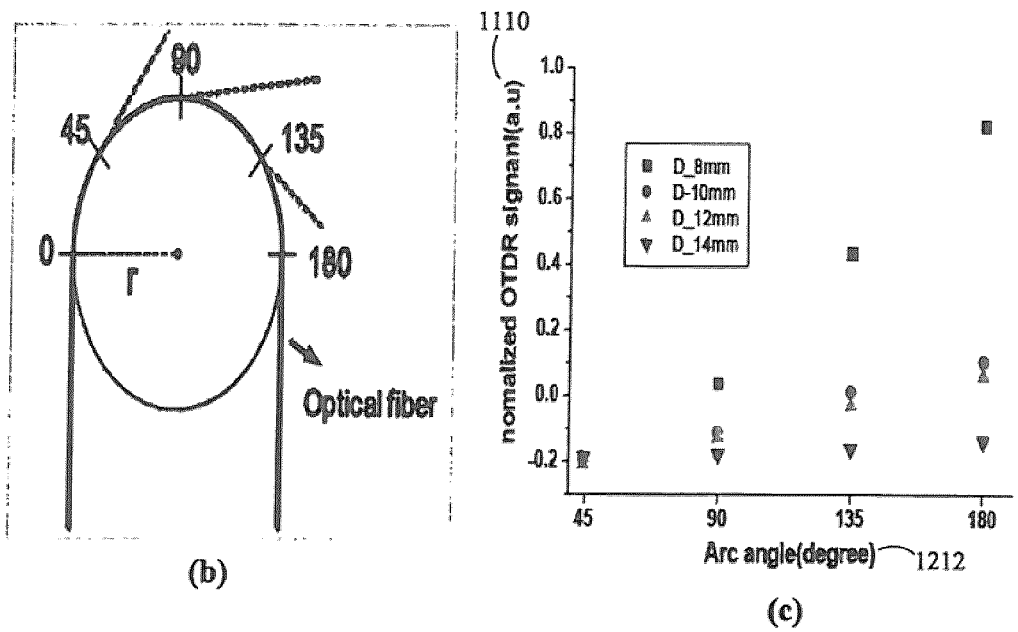
FIG. 12
Kwon, Il-Bum, et al. "Multiplexed fiber optic OTDR sensors for monitoring of soil sliding." *XVIII Imeko World Congress Metrology for a Sustainable Development September, 17–22, 2006, Rio de Janeiro, Brazil.* 2006.
*Understanding OTDRs.* Issue 1. Anritsu Corporation Nov 2011

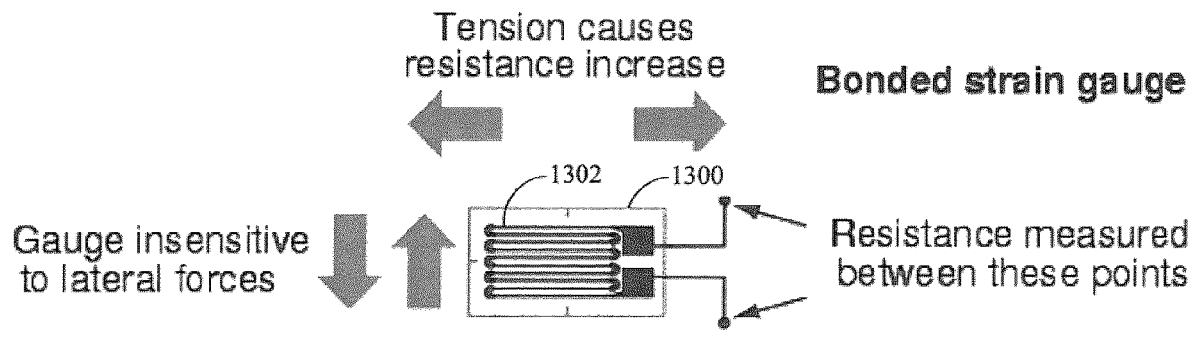
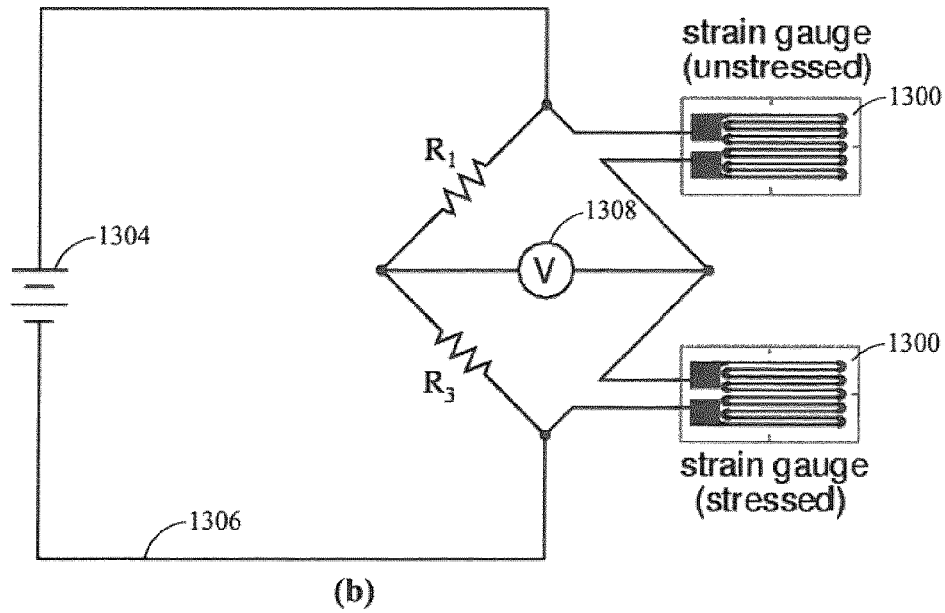
FIG. 13
Starck, Jason. "Strain Gauges." *All About Circuits Forum RSS*. N.p., 2014. Web. 13 Nov. 2014.

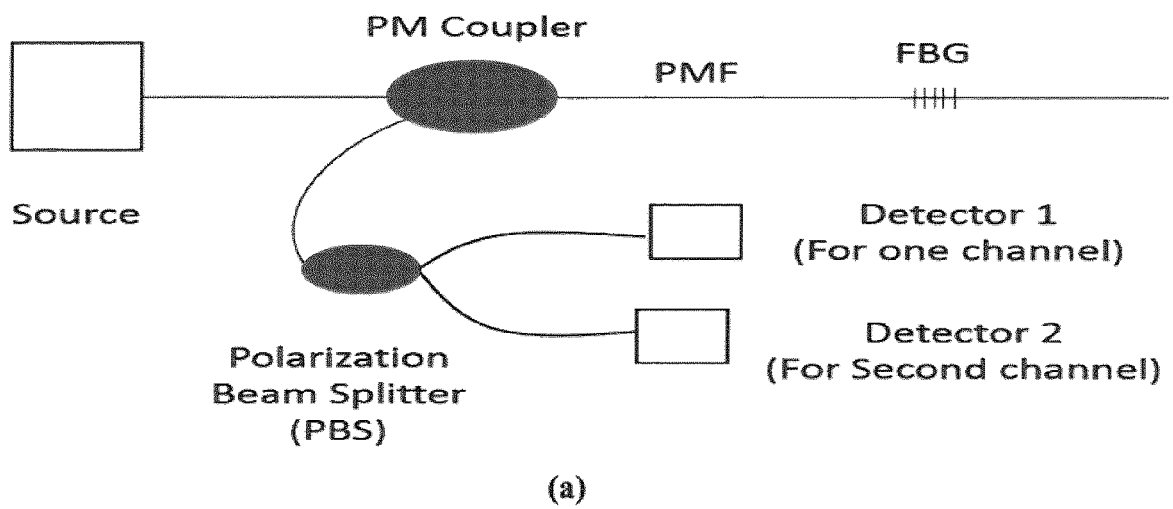
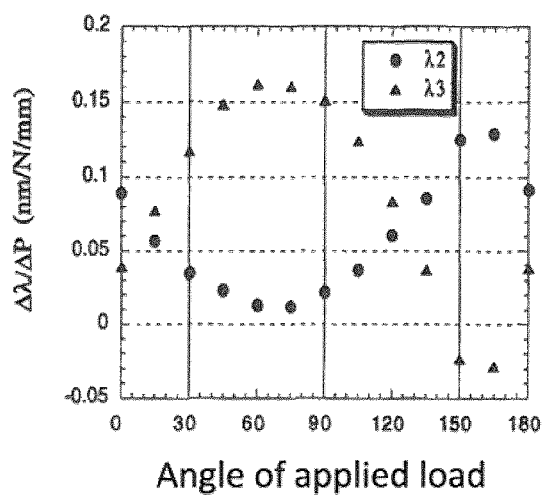
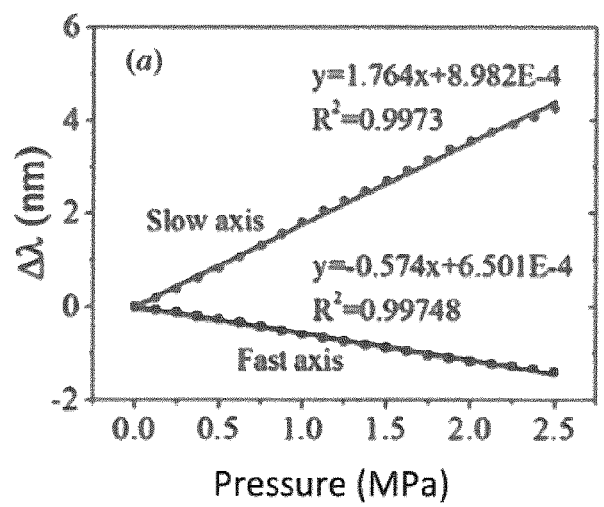
FIG. 14
C. M. Lawrence et al., "A Fiber Optic Sensor for Transverse Strain Measurement," *Experimental Mechanics* 39 (3), 202 (1999)

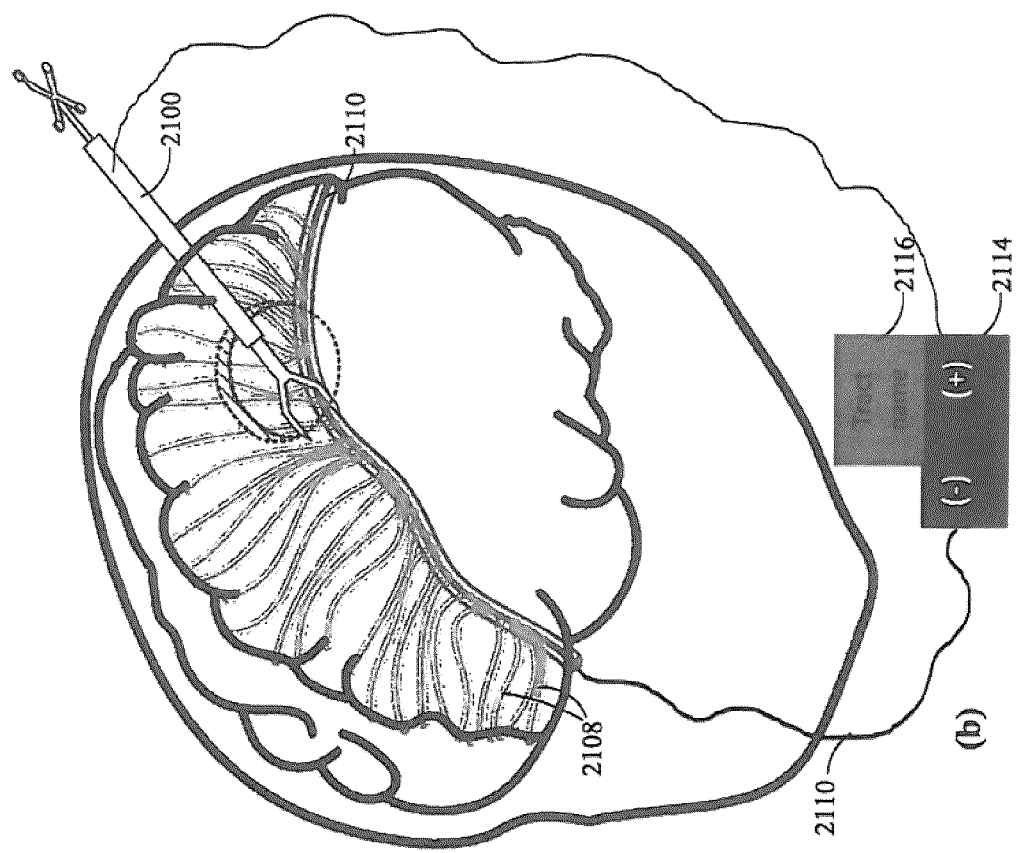
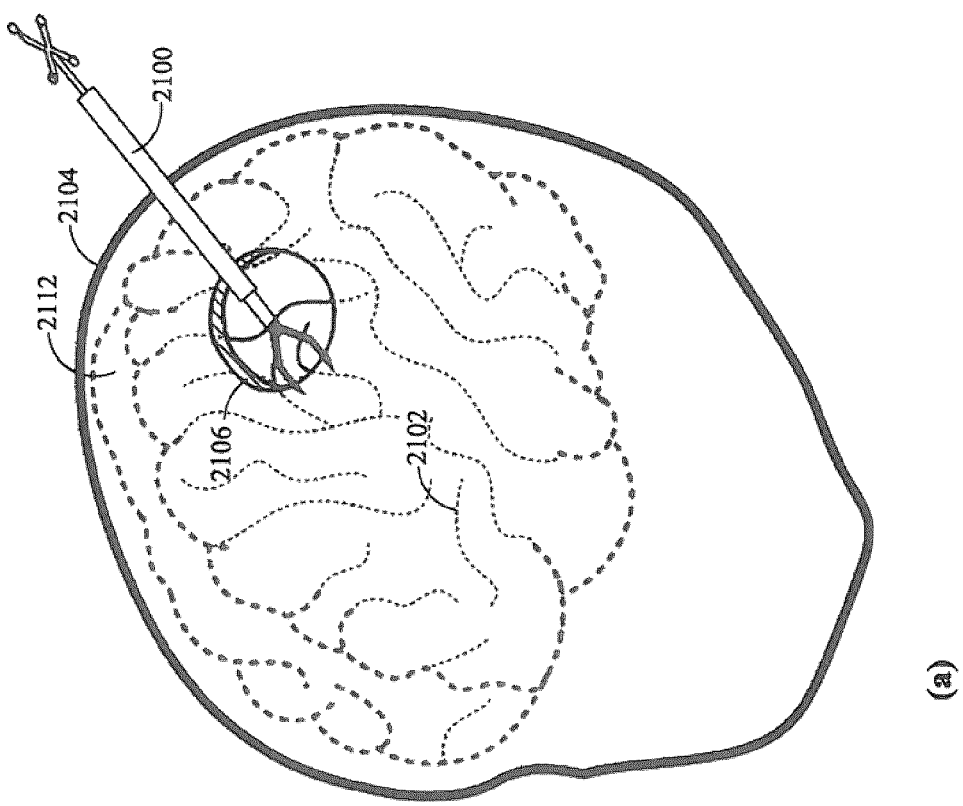
FIG. 21

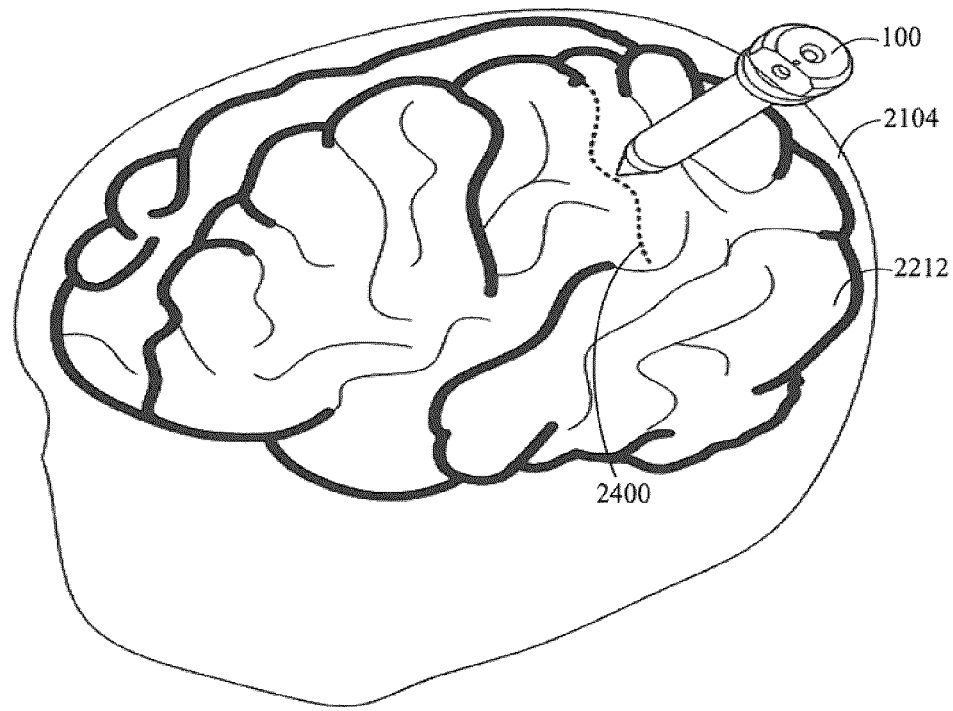
(a)
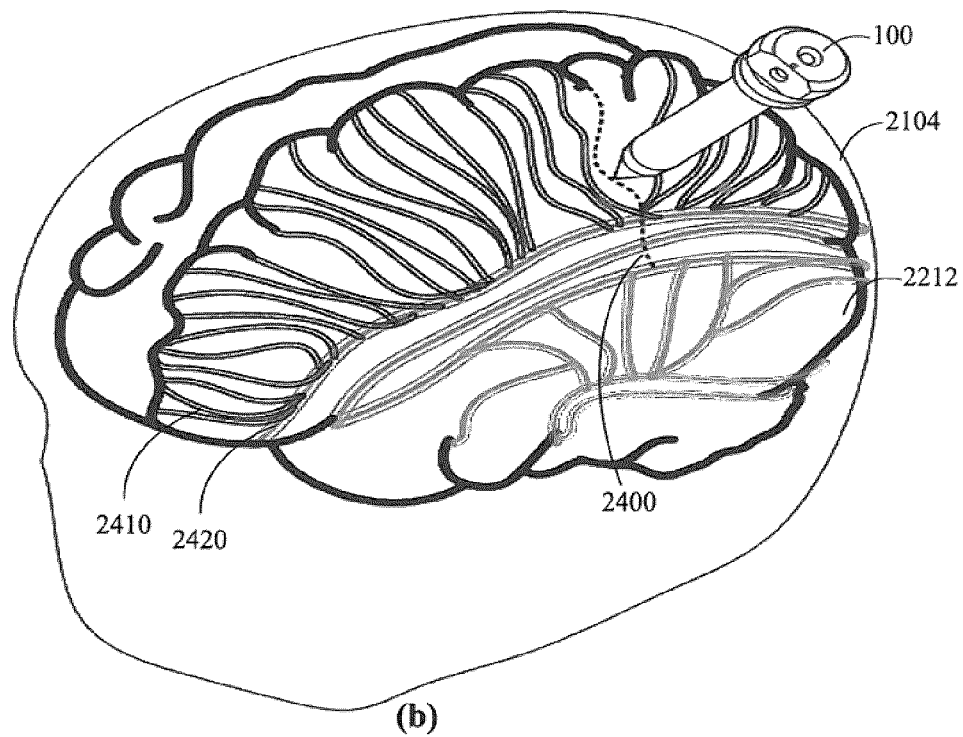
(b)
FIG. 24

PHYSIOLOGICAL PHANTOMS INCORPORATING FEEDBACK SENSORS AND SENSING MATERIALS

FIELD

The present disclosure relates to sensorized medical, imaging and surgical training phantoms.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures, and blood vessels when used in conjunction with an intra-venous agent such as an iodinated contrast agent. MRI may also be performed using a similar contrast agent, such as an intravenous gadolinium based contrast agent which has pharmaco-kinetic properties that enable visualization of tumors, and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices.

Increasingly, functional brain simulators or brain phantoms with fine detail of functionality and structure of the brain can be created with such materials as cryogel. Further, combining phantoms with diffusion tracks and/or with diffusion tensor imaging (DTI) allows realistic navigation paths and resection scenarios to be planned.

Thus, there is a desire to integrate sensors, utilize novel materials and imaging techniques with brain phantoms to provide feedback to surgeons regarding the successful execution of their simulated surgical procedures.

SUMMARY

The present disclosure discloses physiological phantoms incorporating sensors providing a feedback metric (to the user) embedded in a biomechanical mimic of tissue of an anatomical part also known as a tissue phantom. The sensors include, but are not limited to optical fibers containing Fiber Bragg Gratings (FBG), electrical circuits, fiber optic channels, and material substances. The sensors may be sensitive to exposures resulting from but not limited to strain, thermal changes, light, electricity, and etc. such as occurs during medical procedures in which a surgeon is performing a surgical intervention using a medical device such as, but not limited to, a scalpel, a needle, a deep brain stimulation probe, a stimulation probe, a stimulation electrode, an optical device, an access port used in brain or spinal surgery or any part of the mammalian anatomy containing tissue.

The sensors may be interrogated to provide metrics related to the actions being performed on the tissue phantom. These metrics may be reflective of the success of a mock procedure being performed on the tissue phantom.

For example in a tissue phantom employing embedded fiber Bragg grating sensors, when a strain is applied to a portion of the tissue phantom, the optical fibers will undergo strain causing a shift in the reflection spectra from the Bragg gratings in the vicinity of the strain which is detected by the detector, with the amount of the spectral shift being proportional to the amount of strain experienced by the fiber at that location.

The example embodiment of the anatomical (tissue) phantom as disclosed herein containing small diameter optical fibers containing strain sensitive Bragg gratings are useful in many applications. For example, the fibers may be used to emulate brain tracts in a generic brain phantom. Such generic brain phantoms may be used as general training aids for surgical residents and/or medical students.

They may also be used to represent brain tracts of particular importance or relevance in a particular patient. For example, a brain phantom may be produced for a specific patient with a neurological condition requiring medical intervention. In such a case a lifelike brain phantom is produced based on pre-operative imaging acquired by any one or combination of imaging techniques. The optical fibers are then positioned in the parts of the brain phantom most relevant to the medical procedure (e.g., those adjacent to or along a surgical path) during the process of constructing the life-like phantom. This life-like phantom can then be used by the clinician(s) to practice the anticipated medical procedures for that particular patient. In an alternative embodiment, the optical fibers are used to simulate nerve fibers and detect applied pressure and movement in a spinal surgery phantom.

The optical fibers containing strain sensitive Bragg gratings may be used to represent specific types of oriented tissue, including but not limited to tendons, ligaments, directional tissue and the like. For larger structures, in an embodiment of the tissue phantom disclosed herein enables one to detect the displacement of structures such as natural lumens, such as for example blood vessels (veins, arteries), by affixing the optical fibers on the outside or inside of the natural lumens. Note that the fibers may be affixed to any anatomical phantom part, such as any organ, to detect displacement of same during a medical procedure.

A particular advantage of the present phantoms incorporating fiber Bragg gratings for strain detection is that they are optically based. Thus, phantoms constructed as disclosed herein may be used in conjunction with real-time MRI based techniques. Particularly, for phantoms constructed to be used for emulating patient MR imaging, the high magnetic fields will not interfere with the optical signals, unlike electrical based sensors, such as described by additional embodiments of the tissue phantom as disclosed herein, that may be embedded in the phantom. Specifically, brain phantoms can be produced for practicing imaging and include structural features that show up in MR images. In such phantoms optical fibers may be aligned with and affixed with these structural features so that when practicing medical procedures, strain may be detected in fibers and correlated with the MR images of the strained/displaced optical fibers.

A further understanding of the functional and advantageous aspects of the invention can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which:

FIG. 6 (b) is a diagram showing a generic strain detection feedback systems function.

FIG. 6 (c) is a diagram showing a wavelength multiplexed strain detection feedback system.

FIG. 6 (d) is a diagram showing an intensity division multiplexed strain detection feedback system.

FIG. 6 (e) is a diagram showing two OTDR based strain detection feedback systems.

FIG. 7 (b) is a diagram showing a spatially division multiplexed strain detection feedback system.

FIG. 7 (c) is a diagram showing an electrical strain detection feedback system.

FIG. 8 (b) shows the core refractive index of the fiber Bragg grating of FIG. 8 (a).

FIG. 8 (c) shows a typical spectral response of the fiber Bragg grating of FIG. 8 (a) showing the input light and the transmitted and reflected light signals.

FIG. 12 (a) shows an OTDR signal trace.

FIG. 12 (b) shows a bending optical fiber.

FIG. 12 (c) shows an OTDRs signal trace response dependence on bend angle, Kwon, Il-Bum, et al. "Multiplexed fiber optic OTDR sensors for monitoring of soil sliding" XVIII Imeko World Congress Metrology for a Sustainable Development Sep. 17-22, 2006, Rio de Janeiro, Brazil. 2006; and Understanding OTDRs. Issue 1. Anritsu Corporation November 2011.

FIG. 13 (a) is a diagram of an electrical strain gauge, see Starck, Jason. "Strain Gauges." All about Circuits Forum RSS. N.p., 2014. Web. 13 Nov. 2014.

FIG. 13 (b) is a diagram of an electrical strain gauge circuit, see Starck, Jason. "Strain Gauges." All about Circuits Forum RSS. N.p., 2014. Web. 13 Nov. 2014.

FIG. 14 (a) is an illustration of a polarization maintaining fiber Bragg grating system; see C. M. Lawrence et al., "A Fiber Optic Sensor for Transverse Strain Measurement," Experimental Mechanics 39 (3), 202 (1999).

FIG. 14 (b) is an illustration of the angle dependent response of a polarization maintain fiber Bragg grating.

FIG. 14 (c) is an illustration of the angle dependent response of a photonic crystal fiber Bragg grating.

FIG. 15 (b) is an illustration of a combined multiplexing systems of fiber Bragg grating sensors and electrical sensors.

FIG. 18 (ii) is an illustration of a shape sensing strain gauge array.

FIG. 21 (a) depicts the sulci of the brain through a mock craniotomy and mock skull and a stimulation probe inserted through one of the sulci into the brain phantom.

FIG. 21 (b) shows the internal structures contained within the brain phantom matrix material which replicate the tractography of the brain.

FIG. 24 (a) shows the mock surgery before an access port is inserted into a sulcus of a mock brain.

FIG. 24 (b) is an illustration of the progressing intraoperative brain phantom of FIG. 24 (a) showing the built-in feedback network for a mock tumor resection procedure and shows the internal structures contained within the brain phantom matrix material which replicate the tractography of the brain.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

As used herein, the term "patient" is not limited to human patients and may mean any organism to be treated using the planning and navigation system disclosed herein.

As used herein the phrase "surgical tool" or "surgical instrument" refers to any item that may be directed to a site along a path in the patient's body. Examples of surgical tools may include (but are not necessarily limited to) scalpels, resecting devices, imaging probes, sampling probes, catheters, or any other device that may access a target location within the patient's body (or aid another surgical tool in accessing a location within a patient's body), whether diagnostic or therapeutic in nature.

Since image-guided medical procedures are complex in nature and the risk associated with use of such procedures in the brain is very high, the surgical staff must often resort to performing a simulated rehearsal of the entire procedure. Unfortunately, the tools and models that are currently available for such simulated rehearsal and training exercises typically fail to provide a sufficiently accurate simulation of the procedure.

Understanding and modeling tissue deformation is important for surgeons practicing invasive medical procedures on patients. Being able to accurately model how various types of tissue deform will enable surgeons to approach targets in the patient's body with minimal damage to important tissue. Being able to produce tissue phantoms which exhibit biomechanical and imaging characteristics resembling those of patients is a necessary first step in providing a viable life-like tissue phantom on which to practice medical procedures.

Figure 1:
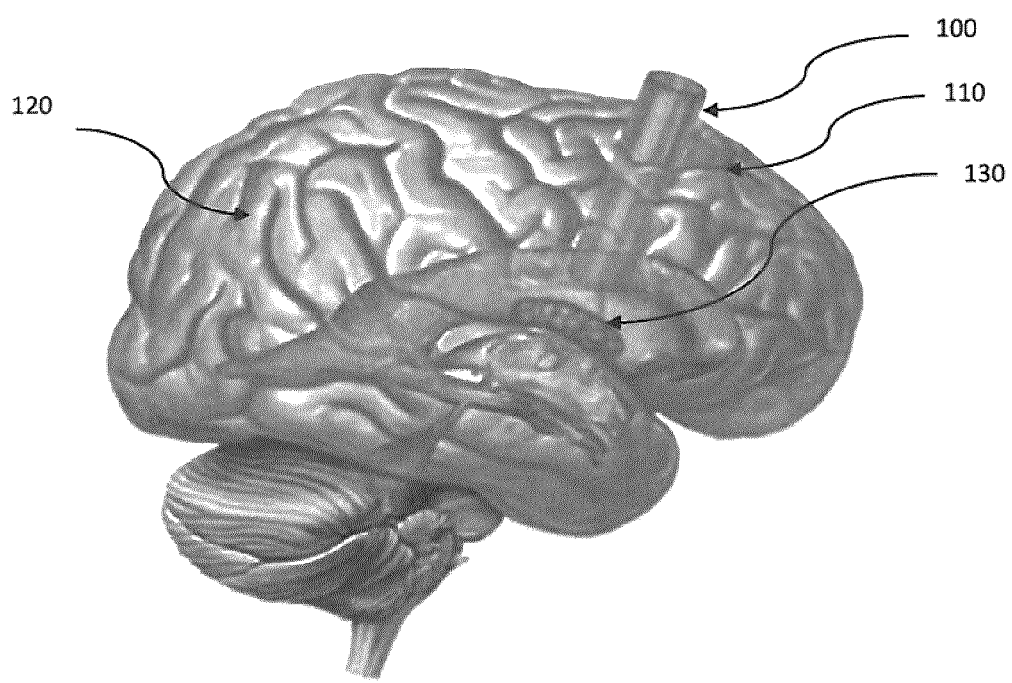
FIG. 1 is an illustration of an example port-based surgical approach in which a port is inserted along the sulci to approach a tumor located deep in the brain.

When performing surgical and/or diagnostic procedures that involve the brain, neurosurgical techniques such as a craniotomy, or a minimally invasive procedure such as an endo-nasal surgery or a port based surgical method, may be performed to provide access to the brain. In such procedures, as indicated, the medical procedure is invasive of the mammalian head. For example, in the port-based surgical method illustrated in FIG. 1, a generally cylindrical port 100 or corridor is inserted along the sulci 110 of the brain 120 to access a tumor 130 located deep in the brain 120. The cylindrical port 100 provides the surgeon with access to the interior portion of the patient's brain being operated on.

According to embodiments provided herein, the simulation of such procedures may be achieved by providing a brain model that is suitable for simulating the medical procedure through one or more layers of the head. Such a procedure may involve perforating, drilling, boring, punching, piercing, stimulating, ablating, resecting, or any other suitable methods, as necessary for an endo-nasal, port-based, or traditional craniotomy approach. For example, some embodiments of the present disclosure provide brain models comprising an artificial skull layer that is suitable for simulating the process of penetrating a mammalian skull. As described in further detail below, once the skull layer is penetrated, the medical procedure to be simulated using the training model may include further steps in the diagnosis and/or treatment of various medical conditions. Such conditions may involve normally occurring structures, aberrant or anomalous structures, and/or anatomical features underlying the skull and possibly embedded within the brain material.

In some example embodiments, the brain model is suitable for simulating a medical procedure involving a brain tumor that has been selected for resection. In such an example embodiment, the brain model is comprised of a brain material having a simulated brain tumor provided therein. This brain material simulates, mimics, or imitates at least a portion of the brain at which the medical procedure is directed or focused. The simulation of the above described medical procedure is achieved through simulation of both the medical procedure and the associated imaging steps that are performed prior to surgery (pre-operative imaging) and during surgery (intra-operative imaging). Pre-operative imaging simulation is used to train surgical teams on co-registration of images obtained through more than one imaging methodology such as magnetic resonance (MR), computed tomography (CT) and positron emission tomography (PET). Appropriate co-registration geometrically aligns images from different modalities and, hence, aids in surgical planning step where affected regions in the human body are identified and a suitable route to access the affected region is selected.

Figure 2:
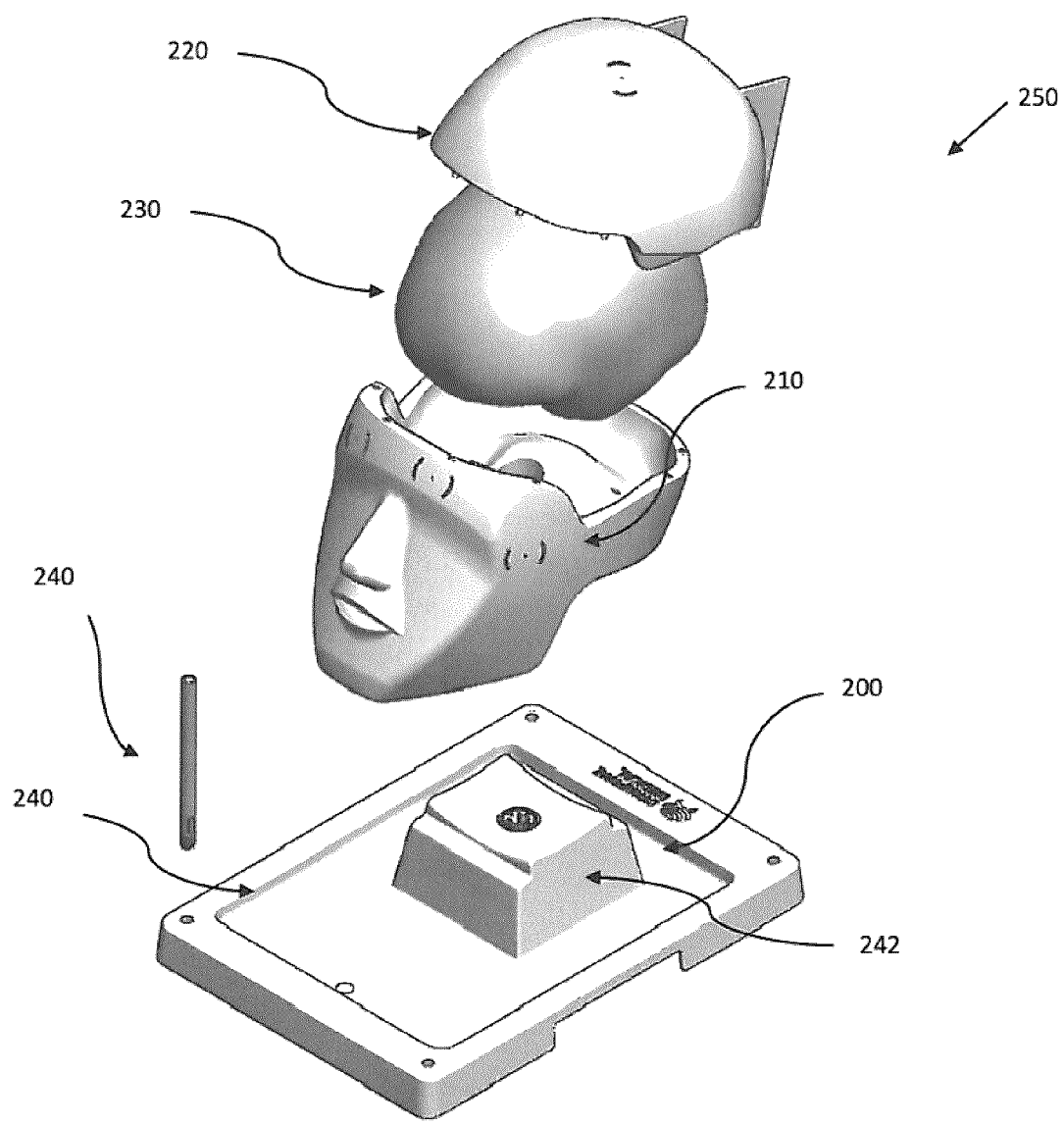
FIG. 2 is an illustration of an example training model head and brain phantom in an exploded view, illustrating parts of the base component and the training component.

Referring to FIG. 2, an exploded view of an example model or phantom shown generally at 250 is provided that is suitable for use in training or simulation of a medical procedure which is invasive of a mammalian head. The training model 250 may be adapted or designed to simulate any anatomical structure. It is to be understood that the person to be trained on the phantom may be selected from a wide variety of roles, including, but not limited to, a medical doctor, resident, student, researcher, equipment technician, or other practitioner, professionals, or personnel. In other embodiments, the models provided herein may be employed in simulations involving the use of automated equipment, such as robotic surgical and/or diagnostic systems. The present disclosure relates to communication channels connected to sensors (such as but not limited to strain sensors) embedded within an anatomical phantom formed from sections of tissue mimic. The sensors may be employed to emulate tissue which can provide information regarding local deformation of the tissue mimic forming the anatomical phantom, during mock medical procedures.

Types of Sensors

There are a multiplicity of sensors or sensing materials that provide a feedback metric to a user of the tissue phantom device as disclosed herein that may suffice for use in the anatomical (tissue) phantoms as disclosed above.

Examples of such sensors or sensing materials include but are not limited to Fiber Bragg Gratings (FBGs), electrical strain gauges, organic semiconductor strain gauges, photo-reactive substances (materials), thermally-reactive substances (materials), electrochromic substances (materials), radiochromic substances (materials), fiber optic channels, polarization maintaining optic fibers, photonic crystal fibers, EM receivers, and etc. The type of strain sensors employed may depend on varying factors such as the communication channel used, the anatomy of the phantom, properties of the tissue phantom material(s), The accuracy level of the sensors, the cost of the sensors, the interaction of the type of sensor with the tissue phantom, the external environment in which the tissue phantom device will be utilized and etc.

In addition each sensor or sensing material type may typically have its own preferred communication channel where applicable for example Fiber Bragg Grating sensors need to be used in combination with optical fibers while electrical sensors may be connected through electrical wires, and organic strain gauges may be connected through a printed flexible circuit or have wireless communication channels, in addition an electro chromic substance (material) may not even require a communication channel. It should be noted before continuing that fiber Bragg gratings will be referred to as FBGs henceforth.

Figure 3:
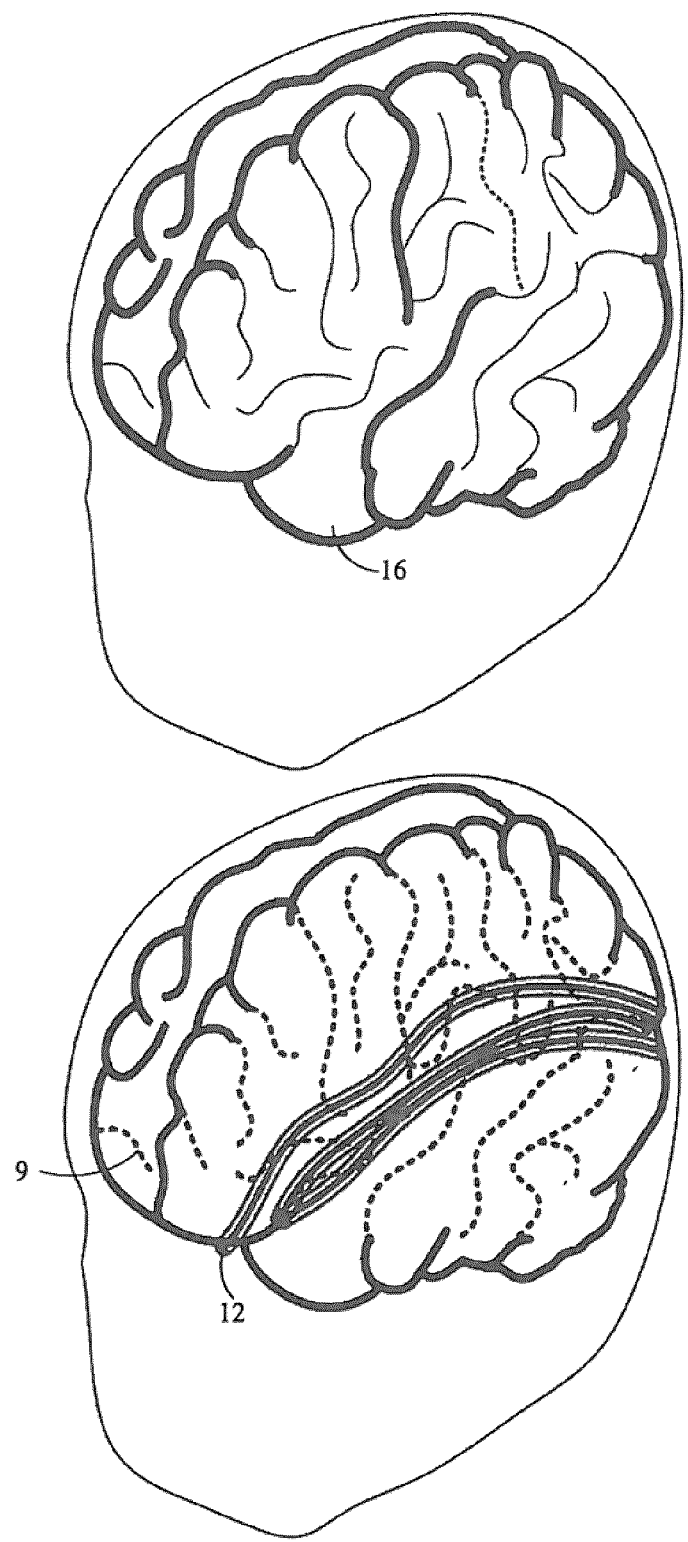
FIG. 3 is an illustration of a brain phantom in a skull having feedback sensors.
Figure 4:
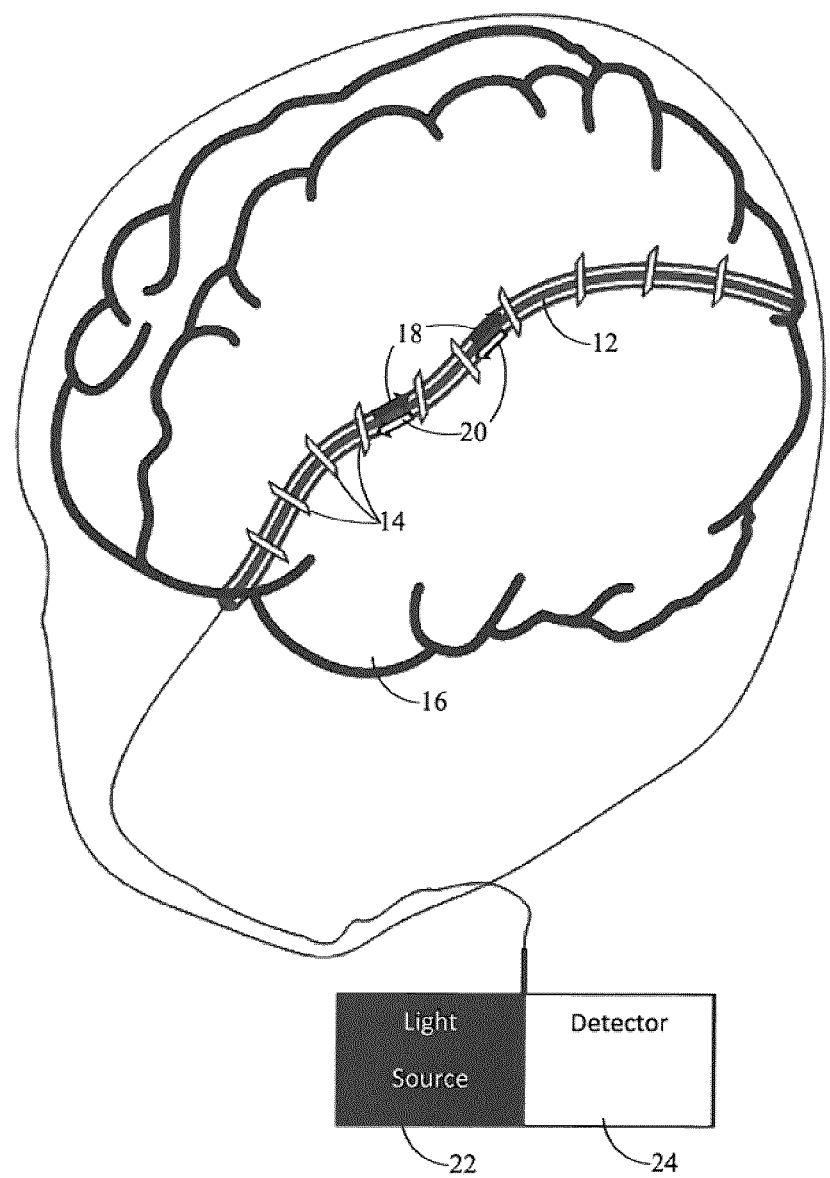
FIG. 4 is an illustration of a fiber optic cable in a brain phantom having fiber Bragg gratings.
Figure 5:
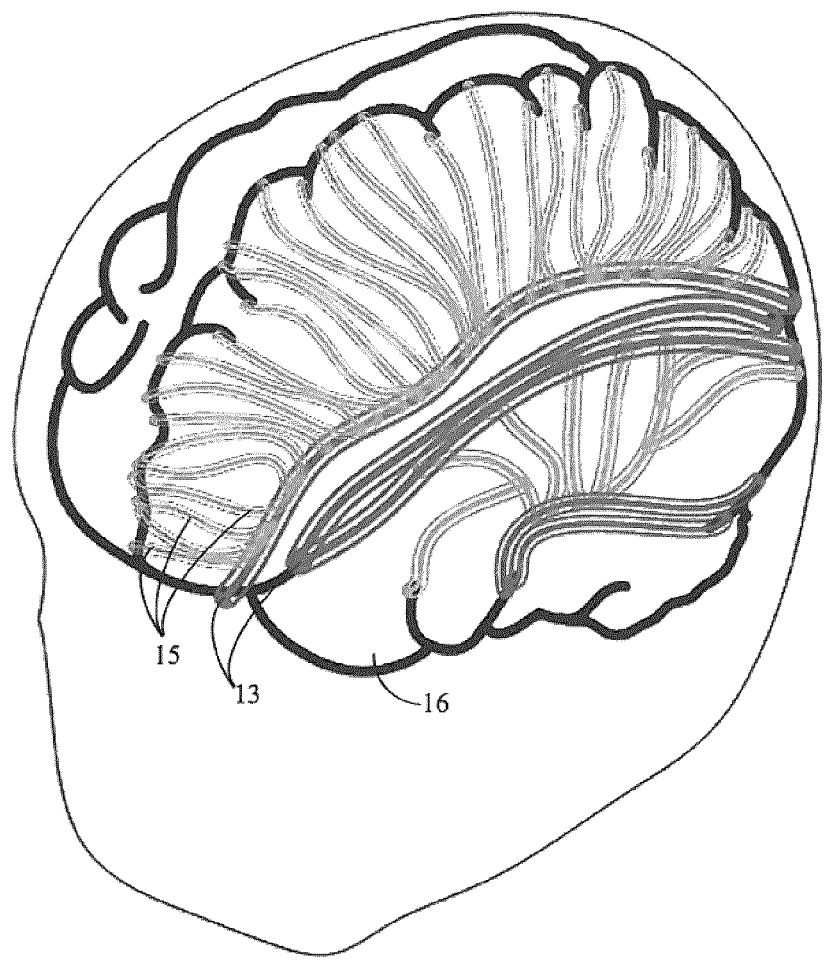
FIG. 5 is an illustration of a brain phantom having a network of feedback sensors.

An embodiment of the device disclosed herein is shown in FIG. 3 to 5 wherein FBG sensors 14 are connected by fiber optic communication channels 12 and are embedded in a brain phantom. The bottom frame in FIG. 3 and FIGS. 4 and 5 depict the inside of the phantom 16, to illustrate this FIG. 3 has dashed lines where the surface is being superimposed on an internal view of the phantom and FIGS. 4 and 5 have no surface texture 9. In general, the device will include the brain phantom 16 shown in FIG. 3 containing a number of optical fibers 12 constructed with a known number of FBGs 14 at known distances along the length of the fibers 12. The known number and distance of the FBGs 14 may be used to locate the source of a detected strain as will be described in further detail below. While typical FBGs suffice for use in most phantoms, in some embodiments small diameter (40-50 microns) optical fibers containing Bragg gratings embedded in tissue phantom material(s) sufficiently small in diameter may be beneficial so as to not induce weakness in the tissue phantom material(s). Nevertheless, the properties of the tissue phantom material(s) can be tailored to compensate for any weakness induced by the presence of the optical fibers 12.

For example, if the tissue phantom is a brain, a useful material is thermally cycled polyvinyl alcohol (PVA) in which the biomechanical properties may be tuned depending on the number of thermal cycles the material is subject to during production of the tissue mimic. Optionally, in an embodiment such as shown in FIG. 5 small diameter optical fibers 15 can represent directional brain tracts which connect various parts of the brain 16, such fibers being of the order of 40 microns in diameter. The fibers may be produced with different Bragg gratings with the different Bragg gratings being employed to designate the different directions of brain tracts, for example brain tracts going front to back (such as the optic tract) in a person's brain 16 may be designated using one type of Bragg grating, brain tracts going from top to bottom 15 in a person's brain may be designated using another type of Bragg grating etc. Alternatively, different Bragg gratings may be used to designate brain tracts on the basis of functionality, not directionality, such as the optic tract 12.

Referring to FIG. 4, there is shown an exemplary strain detection feedback system applied and incorporated as part of a tissue phantom. A tissue phantom may be constructed to emulate any part of a patient's body, animal in general and human in particular. The sensors of the strain detection feedback system in this embodiment are Fiber Bragg Gratings (FBG) comprised of Bragg gratings 14 formed as part of small diameter optical fibers 12. These sensors may be embedded in a tissue phantom material 16 selected to mimic an anatomical part of the patient as shown in FIG. 4. The material of tissue phantom 16 may contain a directional tissue component 18 which may be selected to mimic any one or combination of muscle tissue, ligaments, tendons, white matter brain fiber tracts, nerve bundles, spinal tissue, any natural lumens such as blood vessels and the like. This directional tissue component 12 may be formed of the optical fiber(s) of the strain detection feedback system to simultaneously provide a more accurate biomechanical model as well as feedback for the user, such as a measure of strain along the length of the fibers.

The strain detection feedback system employed in this embodiment is formed of the optical fiber 12 containing the FBG sensors connected to a light source 22, and a detector 24, at the same or alternate ends of the optical fiber 12, for detecting the reflected or transmitted light spectrum of the FBG and inferring a stress dispersion arising from a strain at a FBG embedded in the tissue phantom 16 as described in further detail below.

The basic principle of operation normally used in a FBG based sensor system is to monitor the shift in wavelength of the reflected light relative to the Bragg wavelength. The Bragg wavelength $\lambda_B$ is obtained using $$\lambda_B = 2n\Lambda \tag{1}$$

where $\Lambda$ is the grating period and n is the effective index of the fiber core. The Bragg wavelength shifts through a change of the core effective index and the grating pitch representing varying levels of temperature and strain. The Bragg wavelength shift in response to applied strain $\varepsilon$ is obtained using:

$$\partial\lambda/\partial\varepsilon = \lambda_B(1-p_e) \tag{2}$$

where $p_e$ is the effective photo-elastic coefficient. Given the Bragg wavelength $\lambda_B=1550$ nm and $p_e=0.22$ for fused silica, the strain sensitivity is calculated at 1.21 pm/$\mu\varepsilon$. A diagram of this phenomena is provided in FIG. 8 and described further below.

Using a system of detectors, light sources, and FBGs connected to one or more fibers there exist many interrogation techniques for determining the magnitude and location of strain being imposed on the fiber(s).

In some embodiments, the fiber optic containing the FBG sensors embedded in the tissue phantom material may be deliberately aligned during production of the phantom, to mimic directional tissue components, such as direction muscle tissue, ligaments, tendons, brain tracts etc. This allows for measurement of actual deformation and/or strain at selected locations, and along selected directions, in the tissue phantom as disclosed herein during practice procedures and this may be compared to deformation predicted by tissue deformation models of the phantom as well.

Optical fibers could be threaded though the soft mold in which the brain phantom is produced and supported at specific locations via pins when the phantom is being produced.

Types of Strain Detectors

Figure 6:
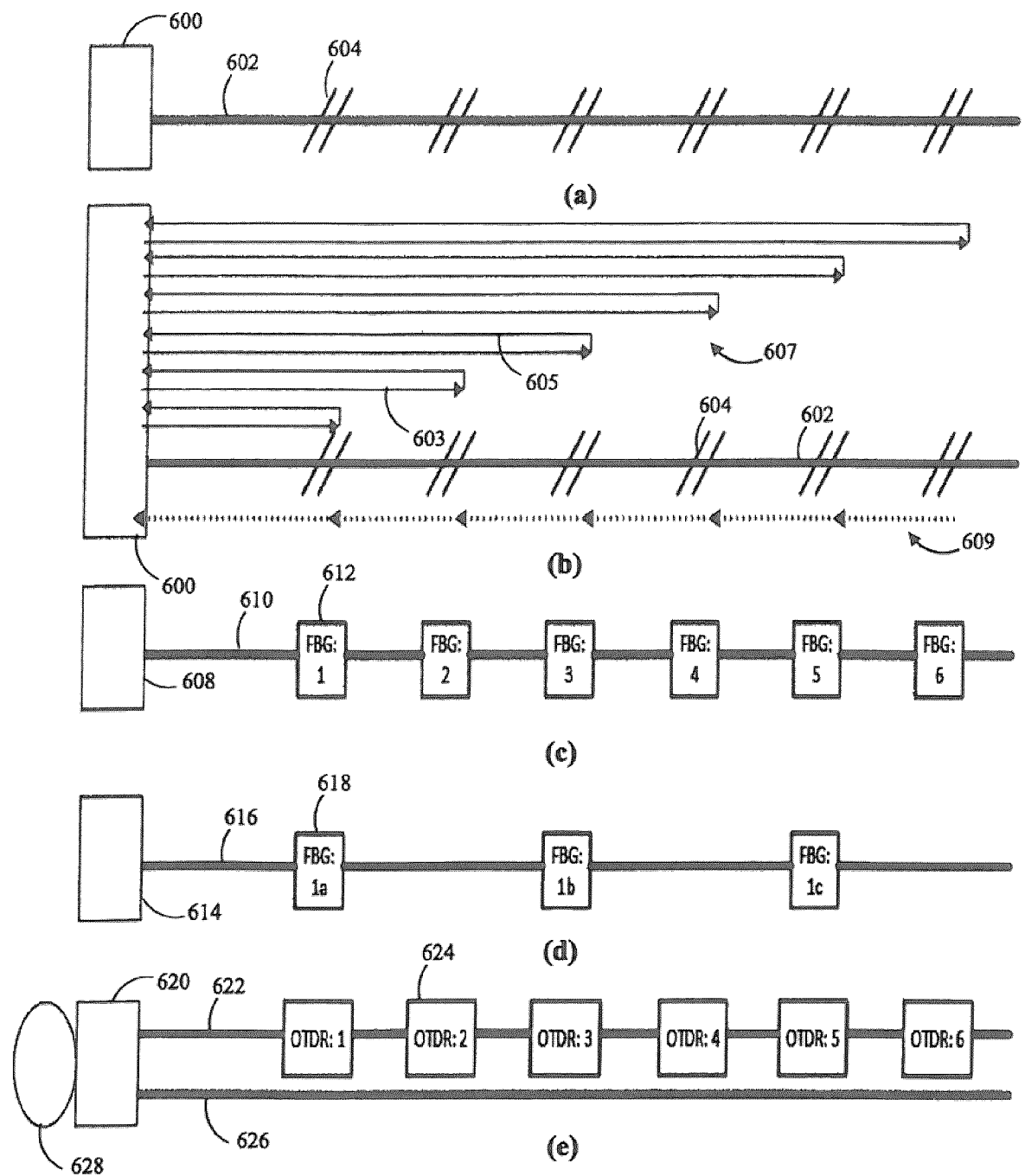
FIG. 6 (a) is a diagram showing a generic strain detection feedback system.
Figure 7:
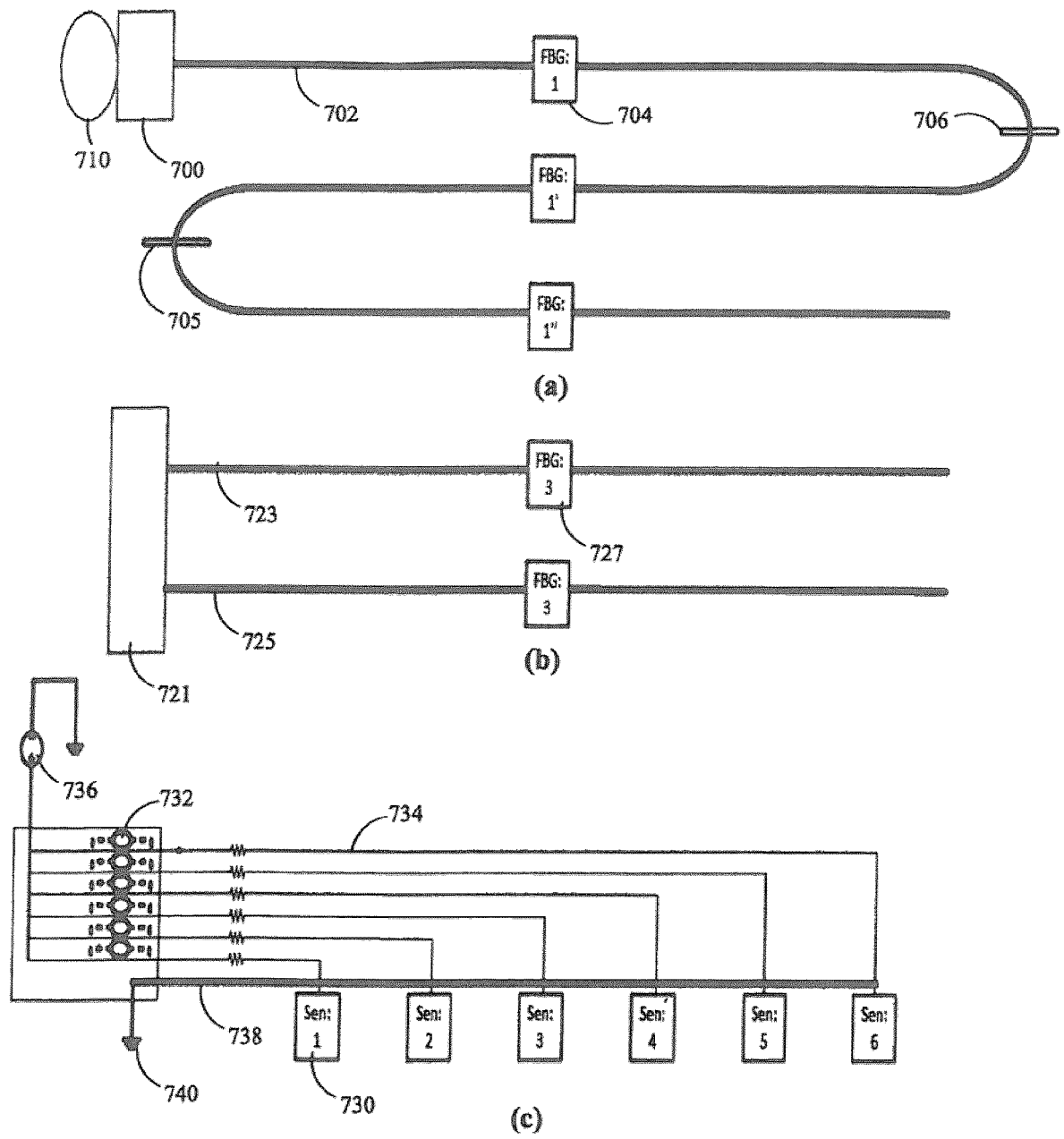
FIG. 7 (a) is a diagram showing a time division multiplexed strain detection feedback system.

Variations of the embodiment described above and depicted in FIG. 5 may be implemented using a multiplicity of strain detectors and detection mechanisms as is depicted in FIGS. 6 and 7, by substituting these strain detection feedback systems for the strain detection feedback system shown in FIG. 4 and described above. These figures show block diagrams of strain detection feedback systems that may be implemented in the tissue phantom device as disclosed herein to allow the detection of strain at various locations on or in the anatomical phantom. The various types of detection feedback systems will be described as follows. It should be noted that any single implementation of a detection feedback system or combination of detection feedback systems thereof may be implemented for use as part of the device disclosed herein. Although most of the detection feedback systems being described are well known in the art these are not to limit the implementations whereby unique systems may arise.

Generic Block Diagram

The first block diagram FIG. 6 (a) shows a generic strain detection feedback system that may be implemented in an embodiment of the device disclosed herein such as that depicted in FIG. 3 to 5 and described above. It follows then that the communication channel 602, strain sensors 604, and detector/source 600 of a generic strain detection feedback system are embodied as a fiber optic communication channel 12, FBGs 14, and an optical detector/optical source 24 respectively in the embodiment shown in FIG. 3 to 5. The light source 22 in the embodiment depicted in FIG. 3 to 5 is a source used to generate an energy signal required to allow the sensors to function. In general a strain detection feedback system may or may not require an energy source depending on the type of sensors chosen.

The diagram FIG. 6 (b) depicts the functioning of a generic strain detection feedback system. In such systems a signal is generally sent from the sensors to the detector to be analyzed against a reference. An example of this system is shown in the section 609 of the diagram FIG. 6 (b). In the diagram the sensors 604 send signals 605 to the detector 600. The detector than analyzes the signal 605 and determines the strain on the particular sensors. In many embodiments these signals may be sent along the same communication channel such as 602 or may be sent along separated channels, such as channels 708a and 708b shown in FIG. 7 (b) or equivalently multiple separate wireless communication channels, or any combination thereof.

Commonly most strain detection feedback systems function by sending an energy signal from a source 600 which is returned to a detector after being altered (including reflecting the signal) in some way by a sensor 604. The return signal is then analyzed in comparison to the initially sent signal or some reference to determine the amount of strain on a particular sensor. An example of this is shown at the top section 607 of FIG. 6 (b). In this example the sent signals 603 are being altered by the sensors 604 depending on the strain applied to them and sent back as return signals 605 to the detector 600 along the communication channel 602. It follows then that the communication channel 602, strain sensors 604, detector 600, signal 603, and return signal 605 of a generic strain detection feedback system are embodied as a fiber optic communication channel 12, FBGs 14, an optical detector 24, and reflected optical return signal 20 respectively in the embodiment shown in FIG. 4.

The light source 22 employed in the embodiment depicted in FIG. 4 may emit an optical signal 22 of variable bandwidth and wavelength 18 which is partially or fully reflected, at the Bragg wavelength, in the form of an optical return signal 20 by FBGs 14 to the optical detector 24 where the signal is then analyzed to determine the amount of strain applied to the specific strain sensor. It should be noted that any light source and detector required in the embodiments of the tissue phantom as disclosed herein may be in the form of a broadband, tunable band, or tunable wavelength source or detector and maybe used in any combination thereof to meet the requirements of the strain detection feedback system as is known in the art.

It is noted that there may be several sources of strain being indicated by the sensors during the mock surgical procedure for several reasons. The main one is by the clinician physically contacting the sensor section or fiber and causing strain by the surgical tool in contact with the sensors. It may also arise due to phantom material in close proximity to the sensor being displaced by the surgical tool into contact with the sensor.

The generic apparatus and generic principle function of strain detection feedback systems as shown in FIG. 6 (a) and FIG. 6 (b) have specific implementations reliant on the choice of hardware employed by the strain detection feedback system. However in order for a strain detection feedback system to uniquely locate its strain sensors positions and their respective strain magnitudes, the hardware typically is designed for integration with a complementary interrogation technique. There are many combinations of interrogation techniques and hardware which may be used to form a multitude of strain detection feedback systems which are well known to those skilled in the art.

Figure 16:
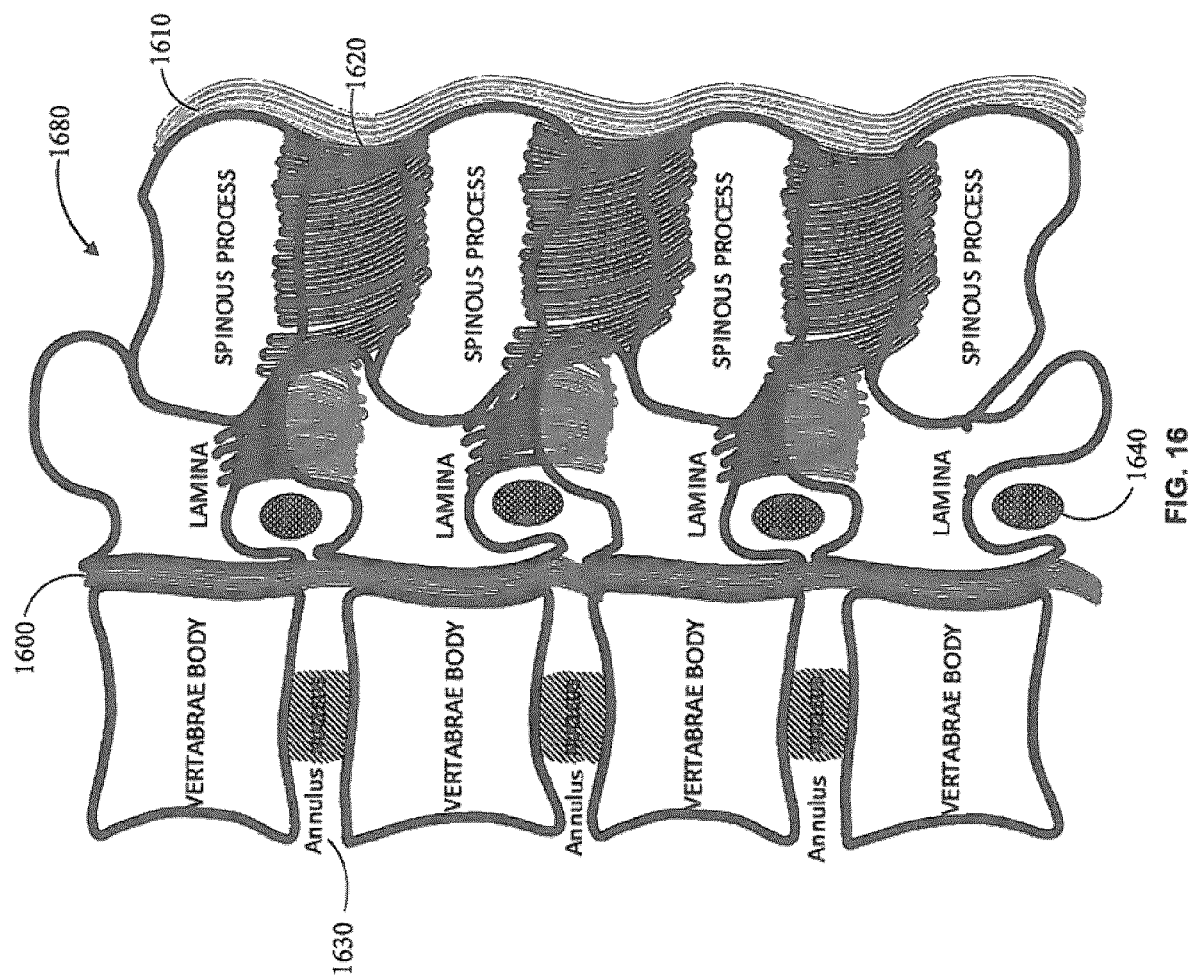
FIG. 16 is an illustration of a spinal phantom with intergrated feedback systems.

Some examples of strain detection feedback systems that may be employed in the tissue phantom disclosed herein are described in detail as follows. It should be noted that any strain detection feedback system as described may be implemented as part of the device disclosed herein to form a phantom integrated with a strain detection feedback system. In particular embodiments any of the strain detection feedback systems described as follows may be integrated into a phantom such as shown in FIGS. 3 and 16. In addition the strain detection feedback systems which will be described are provided as examples of the embodiments of the tissue phantom device as disclosed herein employing strain detection feedback systems only and are not to be interpreted as limiting embodiments of the tissue phantom device as disclosed herein. It should also be noted that the detection of strain need not be limited to providing a magnitude of strain and may be construed as any indication that a strain is being applied on the tissue phantom device as disclosed herein.

Wavelength Division Multiplexing Using Fiber Bragg Gratings

The first strain detection feedback system to be described will be a wavelength division multiplexed system employing FBG strain sensors an example of which is disclosed in the book [Cooper, David J. F. Time Division Multiplexing of a Serial Fibre Optic Bragg Grating Sensor Array; Ottawa: National Library of Canada, 1999. This system may be considered as a further refinement of the embodiment described above in that it has the additional attribute of an interrogation technique. A block diagram of this embodiment is provided in FIG. 6 (c).

Figure 8:
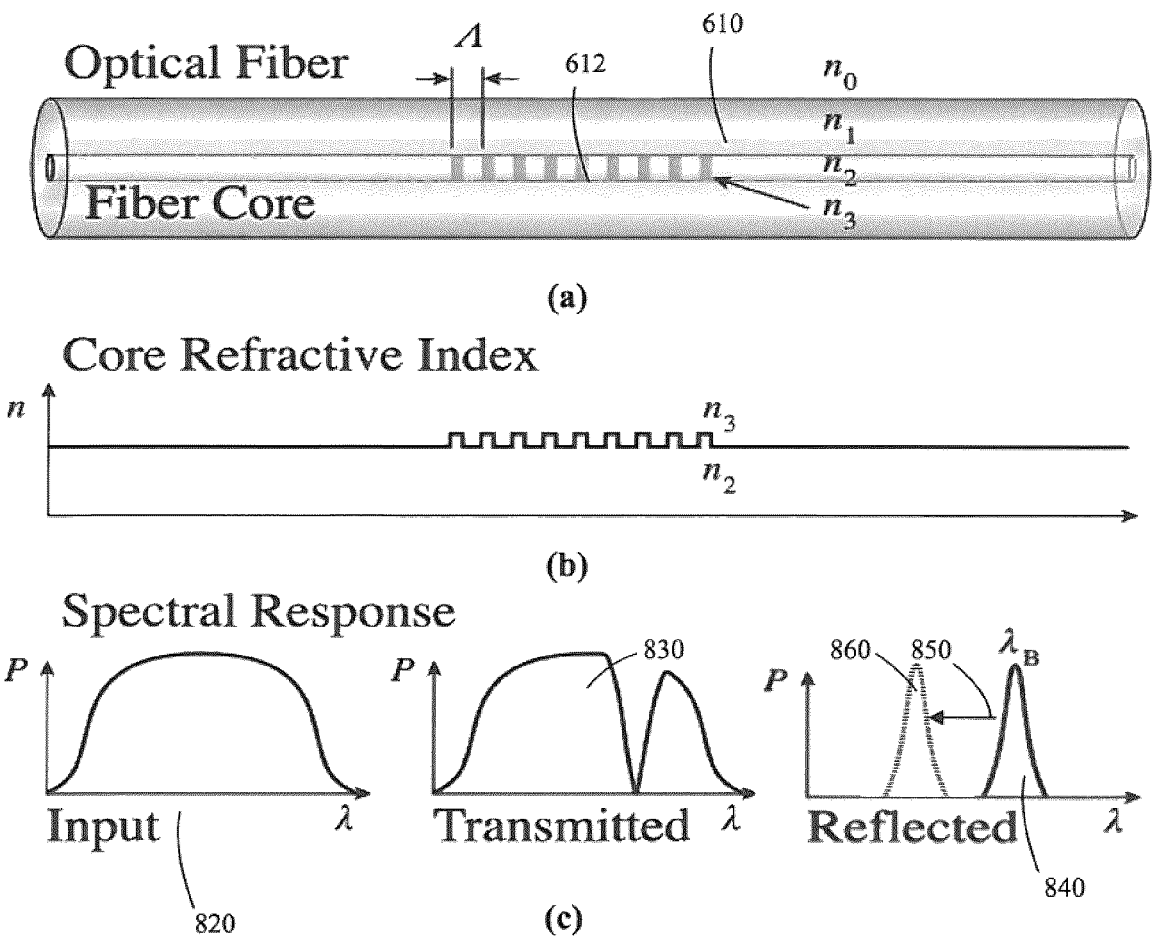
FIG. 8 (a) is a diagram of a fiber Bragg grating.

The principle function of this first strain detection feedback system will be reiterated as follows for clarity with reference to FIG. 8 [Wikipedia contributors. "Fiber Bragg grating." *Wikipedia, The Free Encyclopedia*. Wikipedia, The Free Encyclopedia, 31 Aug. 2014. Web. 14 Nov. 2014.]. This strain detection feedback system embodiment functions by having FBGs 612, formed into a fiber optic channel 610, reflect incoming optical signals 820 (FIG. 8) at a Bragg wavelength back along the channel to the detector 608, while the remaining signal 830 (FIG. 8) is transmitted and continues along the fiber optic channel 610. As the FBGs in this embodiment are placed under strain their Bragg wavelength ($\lambda_B$) shifts 850 according to the following equation $$\Delta\lambda_B = \lambda_{BO}(1-P_e)\varepsilon + \lambda_{BO}(\alpha_\Lambda - \alpha_\eta)\Delta T$$

$$\lambda_{BS} - \lambda_{BO} = \lambda_{BO}(1-P_e)\varepsilon + \lambda_{BO}(\alpha_\Lambda - \alpha_\eta)\Delta T$$

$$\lambda_{BS} = \lambda_{BO}(1-P_e)\varepsilon + \lambda_{BO}(\alpha_\Lambda - \alpha_\eta)\Delta T + \lambda_{BO}$$

Where $\alpha$ and $\alpha_n$ are the thermal expansion coefficient of the optical fiber and the thermo optic-coefficient respectively, $\lambda_{BO}$ (i.e. $\lambda_B = \lambda_{BO}$) is the Bragg wavelength of the FBG under no strain, and $\lambda_{BS}$ (i.e. $\lambda_B = \lambda_{BS}$) is the Bragg wavelength of the FBG under a particular strain. Therefore the wavelength of the reflected signal 860 ($\lambda_{BS}$) from the FBG 612 may be compared to the Bragg wavelength of the FBG under no strain $\lambda_{BO}$ to determine the strain ($\varepsilon$) on the sensor 612 (FIG. 8), given the temperature change is accounted for or held constant throughout.

In this embodiment shown in FIG. 6 (c) the generic communication channel 602, strain sensors 604, and detector 600 of the generic strain detection feedback system are embodied as a fiber optic communication channel 610, FBGs 612, and an optical detector/illumination source 608 respectively.

This embodiment functions in a similar manner to the generic functioning of a strain detection feedback system depicted in FIG. 6 (b). Where the sent signals 603 are being altered by the sensors 604 and sent back as return signals 605 to the detector 600 along the communication channel 602. It follows then that the communication channel 602, strain sensors 604, detector 600, signal 603, and return signal 605 of a generic strain detection feedback system are embodied as a fiber optic channel 610, FBG strain sensors 612, optical detector 608, optical input signal 820, and reflected input signals 860 respectively in the system in FIG. 6 (c).

To ease explanation of the embodiment being described herein henceforth the term "reflection band" will refer to the range of all possible Bragg wavelengths an FBG may reflect incoming light at back to the detector 608, under the influence of any applied strain ranging from no applied strain ($\lambda_{BO}$) to the maximum strain. Where the maximum strain may correspond to the level of strain which would cause the FBG to fracture, the level of strain at the maximum bending amount of the FBG, or an arbitrary predetermined imposed strain limit. In addition the term "original Bragg wavelength" will be used to refer to the Bragg wavelength of an FBG under no strain and the term "altered Bragg wavelength" will be used to refer to the Bragg wavelength of an FBG under an arbitrary level of applied strain.

The interrogation technique of wavelength division multiplexing is applied in this embodiment as shown in FIG. 6 (c) in order to differentiate which sensor 612 (i.e. FBG: 1 . . . FBG: 6) a reflected input signal (return signal) 860 is derived from and determine the magnitude of strain being applied at that specific FBG sensor 612. In order to apply this technique the multiple FBG strain sensors 612 labelled FBG: 1 . . . FBG: 6, must be located at various known locations along the length of the fiber optic cable 610 and must have particular reflection bands. This technique works by segmenting the emission spectrum of the source into intervals (reflection bands) wherein each interval corresponds to a specific sensor. The segmentation is achieved by employing FBGs (FBG: 1 . . . FBG: 6) with original Bragg wavelengths ($\lambda_{BO-1} \ldots \lambda_{BO-6}$) such that the reflection band of that FBG sensor will not overlap with any other FBG sensors reflection band.

Figure 9:
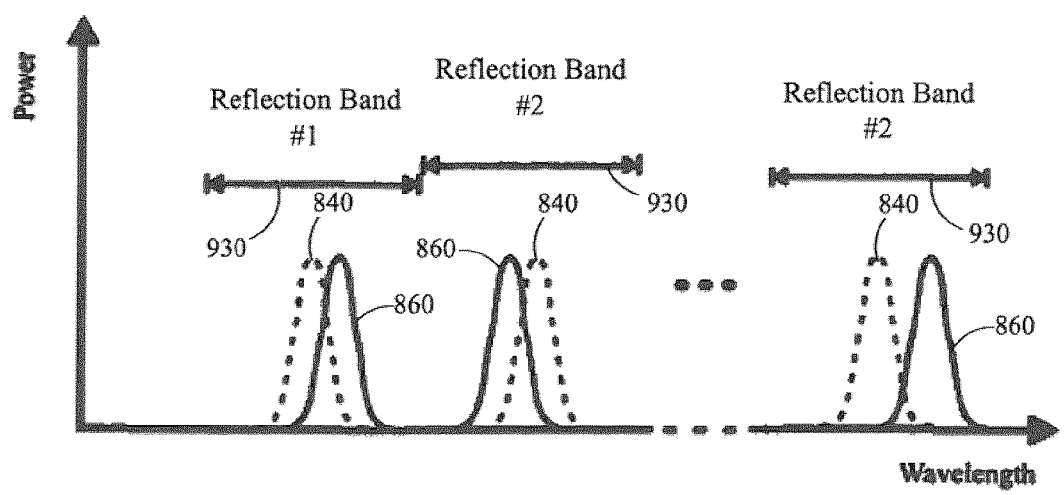
FIG. 9 is a diagram of wavelength division multiplexing (Cooper, David J. F. Time Division Multiplexing of a Serial Fibre Optic Bragg Grating Sensor Array; Ottawa: National Library of Canada, 1999.

An example of this segmentation is depicted in FIG. 9 [Cooper, David J. F.; Time Division Multiplexing of a Serial Fibre Optic Bragg Grating Sensor Array; Ottawa: National Library of Canada, 1999. In the figure there are N reflection bands 930 each one corresponding to a particular FBG sensor 612 with a particular reflection band 930. The intervals depicted by the reflection bands 930 show the range of wavelengths at which an input signal may be reflected and returned to the detector by the FBG. The wavelength of the reflected input signal will be the altered Bragg wavelength 860 of the FBG sensor. The detector 608 may then analyze the reflected input signal to determine its wavelength (or range of wavelengths). Following this determination the wavelength may be used to assign the reflected input signal to a specific FBG sensor (FBG: 1 . . . FBG: 6) depending on which reflection band 930 (0 . . . 6) the wavelength of the reflected input signal falls within. Once assigned a specific FBG sensor the following equation may be used to determine a strain value corresponding to the reflected input signal.

$$\varepsilon = \frac{\lambda_{BS} - \lambda_{BO}}{\lambda_{BO}(1-P_e)} - \frac{(\alpha_\Lambda - \alpha_\eta)\Delta T}{(1-P_e)}$$

Where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 612 (FBG: 1 . . . FBG: 6)) along the fiber optic channel containing the FBGs.

Intensity Division Multiplexing Using Fiber Bragg Gratings

The second strain detection feedback system to be described will be an Intensity division multiplexed system employing FBG strain sensors an example of which is disclosed in U.S. Pat. No. 6,879,742 entitled Using Intensity And Wavelength Division Multiplexing For Fiber Bragg Grating Sensor System. This system is similar to the embodiment described above in that it segments a detectable range (in this case the intensity of the reflected input signal) in order to determine which FBG sensor the reflected input signal was derived from. An exemplary block diagram of this embodiment is provided in FIG. 6 (d). It should be noted that the employed embodiment utilizes FBG sensors (FBG: 1a . . . FBG: 1c) having the same original Bragg wavelengths ($\lambda_{BO1}$) but differing in luminous reflectivity (i.e. percentage of signal at wavelength ($\lambda_{BO1}$) which is reflected).

The principle function of this second strain detection feedback system is identical to that of the first system above where the altered Bragg wavelength ($\lambda_{BS}$) is defined by the following equation $$\lambda_{BS} = \lambda_{BO}(1-P_e)\varepsilon + )\lambda_{BO}(\alpha_\Lambda - \alpha_\eta)\Delta T + \lambda_{BO}$$

Therefore the wavelength of the reflected signal 860 ($\lambda_{BS}$) from the FBG may be compared to the Bragg wavelength of the FBG under no strain $\lambda_{BO}$ to determine the strain ($\varepsilon$) on the sensor 618, given the temperature change is accounted for or held constant throughout.

In this embodiment shown in FIG. 6 (d) the generic communication channel 602, strain sensors 604, and detector 600 of the generic strain detection feedback system are embodied as a fiber optic communication channel 616, FBGs 618, and an optical detector/illumination source 614 respectively.

This embodiment functions in a similar manner to the generic functioning of a strain detection feedback system depicted in FIG. 6 (b). Where the sent signals 603 are being altered by the sensors 604 and sent back as return signals 605 to the detector 600 along the communication channel 602. It follows then that the communication channel 602, strain sensors 604, detector 600, signal 603, and return signal 605 of a generic strain detection feedback system are embodied as a fiber optic channel 614, FBG strain sensors 616, optical detector 618, optical input signal 820 (FIG. 8), and reflected input signals 1000, 1010, and 1020 shown in FIG. 10 respectively in the strain detection feedback system block diagram shown in FIG. 6 (d).

To ease explanation of the embodiment being described herein henceforth the term "intensity band" will refer to the range of all possible luminous intensities (within a tolerance or not) an FBG may reflect incoming light at, back to the detector 608. This "intensity band" will likely be centered on the reflectivity value of the particular FBG wherein the likelihood of an input signal being reflected at a particular luminous intensity may be normally distributed around this reflectivity value as the mean.

The interrogation technique of intensity division multiplexing is applied in the embodiment being described herein as shown in FIG. 6 (d) in order to differentiate which sensor 618 (i.e. FBG: 1a . . . FBG: 1c) a reflected input signal (return signal) 1000, 1010, or 1020 is derived from and determine the magnitude of strain being applied at that specific sensor 618. In order to apply this technique the multiple FBG strain sensors 618 labelled FBG: 1a . . . FBG: 1c, must be located at various known locations along the length of the fiber optic cable 610 and must have specific intensity bands. This technique works by segmenting the intensity detection range into intervals wherein each interval corresponds to a specific sensor. The segmentation is achieved by employing FBGs (FBG: 1a . . . FBG: 1c) with different reflectivity values.

Figure 10:
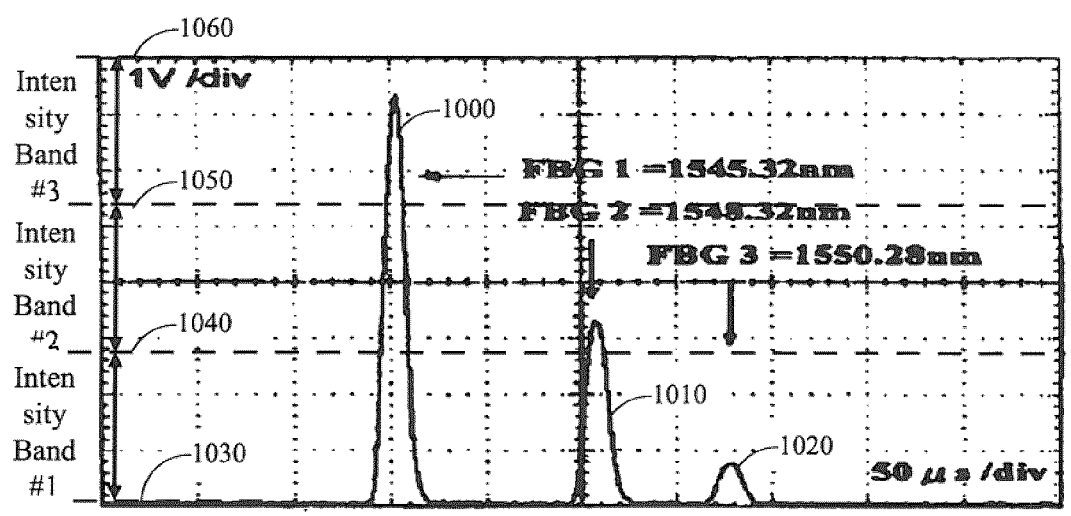
FIG. 10 is a diagram of intensity division multiplexing.

An example of this segmentation is depicted in FIG. 10. In the figure there are 3 intensity bands between the band limits 1030, 1040, 1050, and 1060, each one corresponding to a particular FBG sensor 618 (FBG: 1a, FBG: 1b, and FBG: 1c) with specific intensity bands (intensity band #1, intensity band #2, and intensity band #3 respectively). The intervals depicted by the intensity bands show the range of intensities at which an input signal may be reflected and returned to the detector by a specific FBG. The wavelength of the reflected input signal will be the altered Bragg wavelength 860 of the FBG sensor. The detector 614 may then analyze this reflected input signal to determine its wavelength (or range of wavelengths). Following this determination the intensity range may be used to assign the reflected input signal to a specific FBG sensor (FBG: 1a . . . FBG: 1c) depending on which intensity band the wavelength of the reflected input signal falls within. Once assigned a specific FBG sensor the following equation may be used to determine a strain value corresponding to the reflected input signal.

$$\varepsilon = \frac{\lambda_{BS} - \lambda_{BO}}{\lambda_{BO}(1-P_e)} - \frac{(\alpha_\Lambda - \alpha_\eta)\Delta T}{(1-P_e)}$$

Where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the magnitude of applied strain and the location of that applied strain (i.e. a specific sensor 618).

Time Division Multiplexing Using Fiber Bragg Gratings

The fourth strain detection feedback system to be described will be a time division multiplexed system employing FBG strain sensors. This system is similar to the embodiments described above in that it segments a detectable range (in this case the time of arrival of the reflected input signal) in order to determine which FBG sensor the reflected input signal was derived from. An exemplary block diagram of this embodiment is provided in FIG. 7 (a). It should be noted that the employed embodiment utilizes FBG sensors (FBG: 1, FBG: 1', FBG: 1") having the same original Bragg wavelengths ($\lambda_{BO1}$) and the same reflectivity's (i.e. percentage of signal at wavelength ($\lambda_{BO1}$) which is reflected). The reflectivity of the FBGs in this case must be divided amongst the FBGs such that the percentages accumulate to a maximum of 100% so that the luminous intensity is enough such that it reaches the last sensor with enough luminous intensity to produce a return signal detectable by the detector 700.

The principle function of this fourth strain detection feedback system is identical to that of the first system above where the altered Bragg wavelength ($\lambda_{BS}$) is defined by the following equation $$\lambda_{BS}=\lambda_{BO}(1-P_e)\varepsilon+)\lambda_{BO}(\alpha_\Lambda-\alpha_\eta)\Delta T+\lambda_{BO}$$

Therefore the wavelength of the reflected signal 860 ($\lambda_{BS}$) from the FBG may be compared to the Bragg wavelength of the FBG under no strain $\lambda_{BO}$ to determine the strain ($\varepsilon$) on the sensor 704, given the temperature change is accounted for or held constant throughout.

In this embodiment shown in FIG. 7 (a) the generic communication channel 602, strain sensors 604, and detector 600 of the generic strain detection feedback system shown in FIG. 6 (a) are embodied as a fiber optic communication channel 702, FBGs 704, and an optical detector 700 and illumination source 710 respectively.

This embodiment functions in a similar manner to the generic functioning of a strain detection feedback system depicted in FIG. 6 (b). Where the sent signals 603 are being altered by the sensors 604 and sent back as return signals 605 to the detector 600 along the communication channel 602. It follows then that the communication channel 602, strain sensors 604, detector 600, signal 603, and return signal 605 of a generic strain detection feedback system are embodied as a fiber optic channel 702, FBG strain sensors 704, optical detector 700, optical input signal 820, and reflected input signals respectively in the system shown in FIG. 7 (a).

Figure 11:
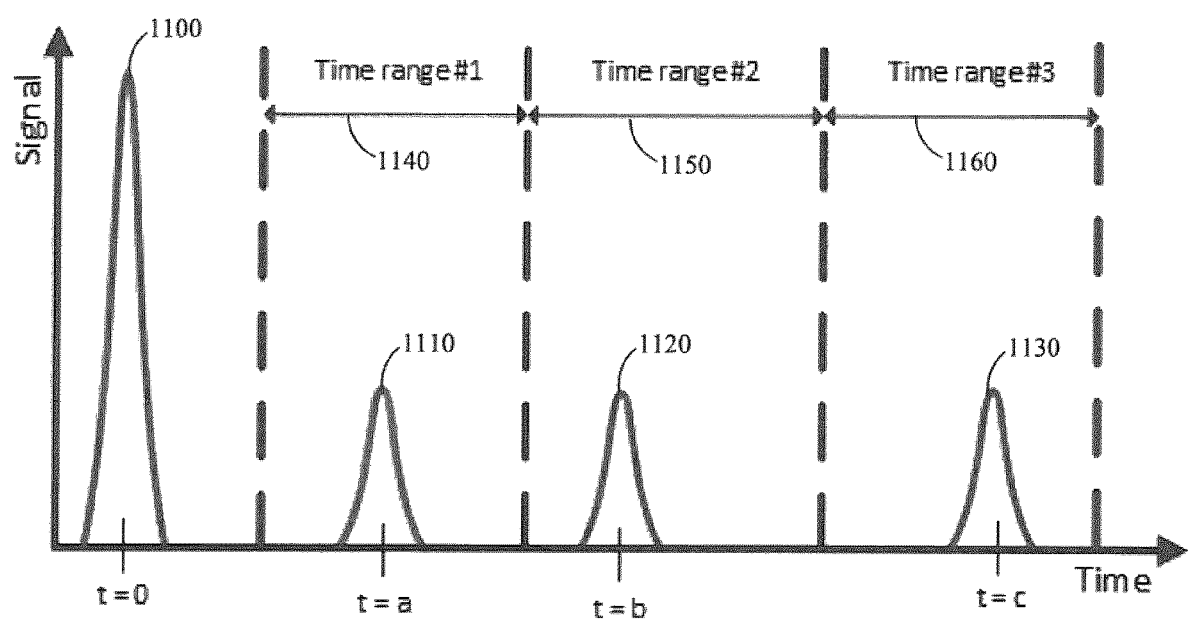
FIG. 11 is a diagram of time division multiplexing.

To ease explanation of the embodiment being described herein henceforth the term "time range" will refer to the interval of time in which all possible reflected input signals by a particular FBG 704 may return to the detector 700 (with or without an error tolerance). This "time range" may be centered on the mean time it would take the initial signal 1100 to return to the detector after emission by the source 710 with upper and lower limits defined by a confidence interval. Wherein it is known to a predetermined confidence, such as a 95%, that the time it takes from initial emission for a signal to be reflected by a specific sensor and return to the detector is in the time interval bounded by these limits. Some exemplary time ranges are shown in FIG. 11.

The interrogation technique of time division multiplexing may be applied in the tissue phantom embodiment as described herein and shown in FIG. 7 (a) in order to differentiate which FBG sensor 704 (i.e. FBG: 1, FBG: 1', and FBG: 1") a reflected input signal (return signal) (1110, 1120, and 1130) is derived from and determine the magnitude of strain being applied at that specific sensor 704. In order to apply this technique the multiple FBG strain sensors 704 labelled FBG: 1, FBG: 1', and FBG: 1", must be located at various known locations along the length of the fiber optic cable 702 and must have specific time ranges. This technique works by segmenting the temporal detection range into intervals wherein each interval corresponds to a specific sensor. The segmentation is achieved by placing the FBGs along the fiber optic channel 702 at specific distances such that the time of flight measurements (amount of time it takes for a signal to travel from the source to the specific FBG and travel back) detectably differ. An example of this segmentation is depicted in FIG. 11. In the figure there are 3 time ranges 1140, 1150, and 1160 each one corresponding to a particular FBG sensor 704 (FBG: 1, FBG: 1', and FBG: 1"). The intervals depicted by the time ranges show the intervals of time after initial emission of a signal 1100 at which a reflected input signal may return to the detector after being reflected by a specific FBG 704. The wavelength of this reflected input signal will be the altered Bragg wavelength of the FBG sensor. The detector 700 may then analyze this reflected input signal to determine its wavelength (or range of wavelengths). Following this determination the time interval may be used to assign the reflected input signal to a specific FBG sensor (FBG: 1, FBG: 1', or FBG: 1") depending on which time range the reflected input signal returns within. Once assigned a specific FBG sensor the following equation may be used to determine a strain value corresponding to the reflected input signal.

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

Where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 704 (FIG. 7 (a))) along the fiber optic channel.

Spatial Division Multiplexing Using Fiber Bragg Gratings

The fourth strain detection feedback system to be described will be a spatial division multiplexed system employing FBG strain sensors. An exemplary block diagram of this embodiment is provided in FIG. 7 (b). It should be noted that the employed embodiment utilizes FBG sensors having the same original Bragg wavelengths ($\lambda_{BO1}$) and the same reflectivity's (i.e. percentage of signal at wavelength ($\lambda_{BO1}$) which is reflected). In this embodiment however there are two communication channels used to differentiate between the FBG sensors.

The principle function of this fourth strain detection feedback system is identical to that of the first system above where the altered Bragg wavelength ($\lambda_{BS}$) is defined by the following equation $$\lambda_{BS} = \lambda_{BO}(1-P_e)\varepsilon + \lambda_{BO}(\alpha_\Lambda - \alpha_\eta)\Delta T + \lambda_{BO}$$

Therefore the wavelength of the reflected signal 860 ($\lambda_{BS}$) (FIG. 8) from the FBG 800 may be compared to the Bragg wavelength of the FBG under no strain $\lambda_{BO}$ to determine the strain ($\varepsilon$) on the sensor 727 (FIG. 7 (b)), given the temperature change is accounted for or held constant throughout. In this embodiment shown in FIG. 7 (a) the generic communication channel 602, strain sensors 604, and detector 600 of the generic strain detection feedback system shown in FIG. 6 (a) are embodied as two fiber optic communication channels 723 and 725, FBGs 727, and an optical detector/illumination source 721 respectively.

This embodiment functions in a similar manner to the generic functioning of a strain detection feedback system depicted in FIG. 6 (b). Where the sent signals 603 are being altered by the sensors 604 and sent back as return signals 605 to the detector 600 along the communication channel 602. It follows then that the communication channel 602, strain sensors 604, detector 600, signal 603, and return signal 605 of a generic strain detection feedback system are embodied as a fiber optic channels 725 and 727, FBG strain sensors 727, optical detector 721, a generic optical input signal, and a generic reflected input signal respectively in the system shown in FIG. 7 (b).

The interrogation technique of spatial division multiplexing is applied in the embodiment being described herein as shown in FIG. 7 (b) in order to differentiate which FBG sensor 727 a reflected input signal (return signal) is derived from and determine the magnitude of strain being applied at that specific sensor 727. In order to apply this technique the two FBG strain sensors 727 labelled FBG: 3, must be located at various known locations along the length of separate fiber optic channels 723 and 727.

In order to apply this technique (i.e. excluding other multiplexing techniques) with N FBG sensors the system would need to employ n=N fiber optic channels. This technique works by identifying which fiber optic channel the reflected input signal is coming from and once known the specific FBG that corresponds to that channel. Determining which fiber optic channel the signal is coming from may be achieved by employing a separate source and detector for each fiber optic channel and connecting the detectors output to a microcontroller programmed to differentiate between the inputs and calculate the strain based on the signals as follows. It should be noted that many optical detectors such as the ones described above are designed using microcontrollers and thus the microcontroller mentioned herein may be superfluous to the separate detectors and the two may be interfaced without an external microcontroller. The wavelength of this reflected input signal will be the altered Bragg wavelength of the FBG sensor. The detector 721 may then analyze this reflected input signal to determine its wavelength (or range of wavelengths). Following this determination the fiber optic channel of the reflected input signal may be used to assign the reflected input signal to a specific FBG sensor depending on which fiber optic channel the reflected input signal was received from. Once assigned a specific FBG sensor, the following equation may be used to determine a strain value corresponding to the reflected input signal.

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

Where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 727).

Optical Time Domain Reflectometry in Fiber Optic Channels

In addition to FBG based strain detection feedback systems there exists other forms of optical strain detection feedback systems that may be used to detect strain or faults within a fiber optic channel. A common example of such a system is an Optical Time Domain Reflectometry system which will be referred to as OTDR henceforth. Two exemplary OTDR system set ups are shown in FIG. 6 (e). The basic set up of such a system is to have a signal source 628 and detector 620 attached to the fiber optic channel (622 or 626) to be monitored.

The bottom channel 626 shown in the figure represents a basic OTDR system. Such a system is described in the report [Understanding OTDRs. Issue 1. Anritsu Corporation November 2011]. An OTDR system functions by injecting a fiber optic channel with an optical signal pulse and measuring the optical signal which is reflected back to the point of injection at discreet time points until the injected signal reaches the end of the channel. Using time of flight calculations and knowing the speed of light in the channel the return signals are then correlated to a specific distance along the channel where they originated essentially creating a signal trace of distance along channel vs. signal.

An example of such a signal trace is provided in FIG. 12 (a). In general the injected signal is reflected back to the detector as a result of two types of phenomena the first being Rayleigh backscattering and the second being Fresnel reflection. Rayleigh backscattering results from the injected signal interacting with impurities (also termed dopants) in the fiber optic cable and scattering in all directions, wherein the signal picked up by the detector is the portion of the scattered signal which was oriented back towards detector. Rayleigh backscattering occurs consistently along the length of the fiber optic cable, additionally the magnitude of interaction is more or less proportional to the strength of the signal at the point (distance along the fiber optic cable) of interaction. With no other phenomenon affecting the injected signal the signal trace should resemble a downward sloping line proportional to the loss in injected signal strength as a result of the continuous Rayleigh backscattering interactions along the length of the fiber optic cable.

An example of an OTDR signal trace is shown in FIG. 12 (a). It is apparent from the figure that the segments 1200 labelled Backscatter Level show characteristic properties of Rayleigh backscattering. Alternatively Fresnel reflection occurs at any points in the fiber optic channel where the injected signal is transmitted from a region of one density to a region with a different density. Fresnel reflection may occur at specific points along the fiber optic cable where such a density shift may occur such as at a splice point, a damaged fiber area, or the end of the fiber optic channel. When the phenomenon occurs on the trace the intensity of the signal which is reflected back is generally much greater than the consistent Rayleigh backscattering occurring in the background. Therefore in the event of a Fresnel Reflection it is common to see a spike on the OTDR trace. Examples of such a spikes are shown as 1204 in the FIG. 12 (a). As is apparent from the figure the signal at beginning and ending of the fiber shown on the left and right sides of the cursors 1202 and 1206 respectively both produce a Fresnel reflection event indicative of the change in density of the medium. Another event that may occur is a sudden loss of signal termed a "point loss" 1208 and characterized by a dip in the Rayleigh backscatter level 1200. Such an event may be indicative of a fusion splice or a stress point in the fiber optic channel where light is escaping.

In order to employ a basic OTDR system in the tissue phantom device as disclosed herein a comparison of an initial signal trace against a signal trace taken after a mock operation is performed on the tissue phantom may be acquired. By subtracting the two traces by using a computer for example any differences will be revealed and may be analyzed to infer if any significant changes to the fiber optic channel such as the ones described above may have potentially occurred. In addition, the magnitude of strain or other force that may have caused such a change may also be determinable given the relative difference of signals at distances along the comparison signal trace.

An alternative strain detection feedback system which employs an OTDR detector and sensor interprets the bend loss in optical fibers to determine the bending angle or equivalent, of the fiber from its initial position. Such a system is depicted in FIG. 6 (e) along the fiber optic channel 610. This system employs a built-in displacement sensor to more accurately measure the strain at specific sensor locations along the length of the channel. To do so the system uses pairs of fiber optic channel integrated mirrors to provide a relative change in the signal strength over an interval of fiber optic channel. The relative change may then be compared to a known table to quantify the amount of bending the channel incurs between the mirrors.

An example of this system is provided in the paper [Kwon, Il-Bum, et al. "Multiplexed fiber optic OTDR sensors for monitoring of soil sliding." XVIII Imeko World Congress Metrology for a Sustainable Development Sep. 17-22, 2006, Rio de Janeiro, Brazil. 2006]. The principle function of this strain detection feedback system will be further elaborated with reference to FIG. 6 (e) along the fiber optic channel 610, FIG. 12 (b), and FIG. 12 (c). Each OTDR sensor 624 shown in FIG. 6 (e) is formed of two fiber optic channel integrated mirrors designed to reflect a percentage of the luminous intensity of an input signal injected at one end of the fiber back to the point of injection. The mirror closest to the source 628 that injects the signal is termed the reference mirror and will provide the reference signal and the mirror further from the source will be termed the sensor mirror and will provide the sensing signal. Both mirrors are designed to reflect the same luminous intensity. The mirrors are oriented around an interval of fiber optic channel that will define the region where the acquired bending angle or equivalent information of the sensor will refer to. FIGS. 12 (b) and (c) show the dependence of the bending angle of the interval on the relative value of the reflected signals by both the reference and sensing mirrors according to the equation provided as follows.

$$\text{Normalized } OTDR \text{ Signal} = C\left\{\left(\frac{V_r - V_s}{V_r}\right)_i - \left(\frac{V_r - V_s}{V_r}\right)_o\right\}$$

Where C is a proportionality constant $$\left(\frac{V_r - V_s}{V_r}\right)_i$$

is the normalized ratio at some time i after the starting ratio $$\left(\frac{V_r - V_s}{V_r}\right)_o$$

is taken at time o. The values depicted with $V_r$ and $V_s$ are the induced detector outputs in arbitrary units by the reflected signals at the detector 620 by the reference and sensor mirrors respectively of the sensor 624. The normalized ratios are used to offset the natural reduction in signal at successive distances along the optical fiber channel resulting from Rayleigh Backscattering and other sources of signal loss. The plot shown in FIG. 12 (c) shows the dependence of the Normalized OTDR Signal, as calculated above, on the rotation angle 1212 of the interval of fiber optic channel contained within the sensor 624. This strain detection feedback system may be employed in an embodiment of the tissue phantom device disclosed herein wherein the bending of the fiber optic channels would be indicative of the amount of strain that those fibers may have been exposed to.

In this embodiment shown in FIG. 6 (e) the generic communication channel 602, strain sensors 604, and detector 600 of the generic strain detection feedback system shown in FIG. 6 (a) are embodied as the fiber optic communication channels 622 and 626, displacement sensors 624, and an optical detector 620 and illumination source 628 respectively.

This embodiment functions in a similar manner to the generic functioning of a strain detection feedback system depicted in FIG. 6 (b) where the sent signals 603 are being altered by the sensors 604 and sent back as return signals 605 to the detector 600 along the communication channel 602. It follows then that the communication channel 602, strain sensors 604, detector 600, signal 603, and return signal 605 of a generic strain detection feedback system are embodied as a fiber optic channels 622 and 626, displacement sensors 624, optical detector 620, optical source 628, an optical input signal, and a reflected input signal respectively in the system shown in FIG. 6 (e).

Electrical Strain Detection Feedback Systems

In addition to optical fiber based strain detection feedback systems there exists other forms of strain detection feedback systems that may be used to detect strain or faults within a tissue phantom. A common example of such a system is an electrical circuit based system such as the system depicted in FIG. 7 (c). Two exemplary electrical system may employ simple ammeter sensors or bonded strain gauge sensors such as those shown in FIG. 12. FIG. 7 (c) shows a generic circuit diagram of an electrical strain detection feedback system as it may be employed in an embodiment of the device as disclosed herein. In general an electrical strain detection feedback system will have a voltage source 736 to power the circuit, electrical communication channels 734 to relay information from the sensors 730, detectors (such as a computer or microcontroller) 732 to interpret an acquired electrical signal from the sensors along the electrical communication channel, and a relative ground 740 as is required for all circuits to function.

In the first exemplary system the sensors 730 are simply connection points at which the communication channels 734 connect to the ground 740 of the circuit. When the connections exist current flows from the voltage source 736 to the ground 740 through the communication channels 734. The detector 732 is an array of ammeters measuring the current flow through each communication channel 734 and are connected to a computer or microcontroller programmed with instructions to provide an indication of which communication channel has an error if any of the communication channel currents drop to zero while the voltage source 736 is on. Thus if a connection is broken, for example through the application of excess strain, the microcontroller will provide information as to which sensor was damaged.

It should be noted that all of the electrical communication channels may be oriented along a single electrical cable with a single ground wire or along individual electrical communication channel cables each with their own ground. If the location of the sensors are known along the length of the electrical communication channel than when an indication is provided that an error has occurred along that channel the location of which channel has been damaged will indicate where excess strain was applied. However if the current of a group off successive electrical communication channels drops to zero and the channels are oriented in a single cable than it may be probabilistically assumed that the channel that the connection that broke was that of the sensor closest to the detectors 732 when the system is oriented in the manner shown in FIG. 7 (c). This results from the sensors 730 being essentially in a serial orientation thus if a lower connection is broken all of the higher connections will be broken as well. This particular embodiment although useful provides no information as to the magnitude of the strain being applied at the point of interest.

The alternate electrical strain detection feedback system embodiment may use electrical bonded strain gauge sensors in place of the connection based sensors as described above. An example of such a sensor is shown in FIG. 13 (a) [Starck, Jason. "Strain Gauges." All About Circuits Forum RSS. N.p., 2014. Web. 13 Nov. 2014]. Bonded strain gauges take advantage of the inherent relationship between the resistance of an electrical conductor and the strain being applied to it. Referring to FIG. 13 (a) as the bonded strain gauge 1300 is exposed to compression or tension along its long axis the electrical conductor increases and decreases in length effectively changing its resistance.

The change in voltage caused by the change in resistance may then be measured and correlated with the change in strain. This embodiment is also illustrated in FIG. 7 (c) the only difference being this embodiment would not require the ammeters 732 hence why they are shown with dashed lines, indicating they are removable. When being used to illustrate this embodiment the sensors 730 in FIG. 7 (c) may be any circuits employing strain gauges, such as the one depicted in FIG. 13 (a), utilized in the form of a sensor to output the strain felt at the location of the sensor. Such a sensor may take the form of the circuit shown in FIG. 13 (b). In the figure two strain gauges 1300 are employed, one may be located on the wire while the other is used to compensate for any temperature related strain response. As strain is detected by the strain gauge on the wire the voltage change caused by the increased or decreased resistance of the electrical strain gauge may be measured by the voltmeter 1308 and output to a microcontroller (not shown). This output may then be converted to a strain reading by the equation provided below and be communicated to the user.

$$\varepsilon = \frac{4v}{BV \cdot GF}$$

Where ε is the strain, v is the voltage read across the bridge of the circuit by the voltmeter 1308, BV is the bridge excitation voltage provided by the source 1304, and GF is the gage factor. It should be noted that the voltage source of the sensor circuit 1304 and ground 1306 in FIG. 13 (b) may be the same as the voltage source 736 and ground 740 of the diagram in FIG. 7 (c). This voltage source and ground may also be common across all sensors (SEN: 1 . . . SEN: 6) in the strain detection feedback system shown in FIG. 7 (c).

Polarization Maintaining FBG and Photonic Crystal Fiber Detection Feedback Systems In addition to the examples described above employing fiber optic channels, many types of optical fiber channels may be utilized. These alternative optical fiber channels may be used in combination with or to substitute for the fiber optic channels of the previous examples where applicable.

Presently FBGs may be integrated into many different optical fibers with the most common ones being single mode and multimode. Some advantages of utilizing single mode fibers include providing optimal light transmission and reflection with the least intensity loss while advantages of utilizing multimode fibers include a large bandwidth for wavelength multiplexing configurations, such as described in detail above.

In addition, FBGs may be made in specialty fibers, including but not limited to polarization maintaining fibers and photonics crystal fibers. Polarization maintaining fibers are optical fibers that allow two orthogonal linearly polarized light beams (of the same or different wavelength) to be propagated and maintained over the entire fiber optic channel length with little or no cross-coupling of optical power between the two orthogonal channels. Polarization maintaining fibers maintain polarization by introducing stress in the fiber core via a non-circular cladding cross-section, or via rods of another material included within the cladding. For example, an elliptical cladding could be used to induce stress in one direction while inducing little or no stress in the orthogonal direction. This essentially creates two orthogonally polarization channels with different refractive indices As a result, each polarization channel may maintain a linearly polarized light beam. In another example, circular or trapezoidal stress rods may be added in the cladding to add stress in only one direction of the fiber, namely Panda Polarization Maintaining fibers and Bow-Tie Polarization Maintaining fibers. Due to the strong birefringence created in the polarization maintaining fiber optic channel by the induced stress, linearly polarized light maintains its polarization state throughout the entire propagation length of the fiber optic channel with little or no perturbation by stress, strain, and temperature fluctuation within the fiber and its surrounding environment.

By integrating FBGs into polarization maintaining fibers, two orthogonal polarization modes in the polarization maintaining fiber optic may reflect at different wavelengths since the effective refractive indices for the two modes are different as a result of the induced birefringence. In each channel, the Bragg wavelength shift induced by a strain change is generally similar to that for a fiber Bragg grating in a single mode fiber. The Bragg wavelength $\lambda_i$ in polarization maintaining fiber is obtained using:

$$\lambda_i = 2n\Lambda \quad (i=X,Y).$$

The advantage of having two orthogonal polarization channels built into a single fiber optic channel is it allows multi-axis strain and temperature sensing. FIG. 14 (a) shows an example strain sensing system in which two detectors and a polarization beam splitter are used to detect the two orthogonally polarized channels in the polarization maintaining fiber optic channel. The reflectivity and wavelength shift changes with the angle of applied load in addition to the strain level. FIG. 14 (b) shows how the wavelength shifts in each polarization channel with respect to the angle and pressure level from as shown in the paper [C. M. Lawrence et al., "A Fiber Optic Sensor for Transverse Strain Measurement," Experimental Mechanics 39 (3), 202 (1999)]. Another advantage of using polarization maintaining fiber optic channel based FBGs is the reduced perturbation to fiber bending and temperature fluctuations at locations where fiber Bragg gratings are not written thus enabling strain sensing to be more accurate, sensitive and more localized to the sensing locations. Furthermore, the previously described multiplexing techniques may also be used with polarization maintaining fiber optic channel based FBG strain detection feedback systems.

Fiber Bragg grating could also be integrated with polarization maintaining photonic crystal fiber channels. Photonic crystal fiber channels, also known as micro-structured optical fibers, photonic bandgap fibers, and holey fibers, are optical fiber channels where light confinement and guidance is carried out using a periodic array of air holes (i.e. photonic crystals) instead of a solid cladding as done in the polarization maintaining fiber optic channel mentioned above. The periodic array of air holes creates an optical bandgap in the cladding that prevents selected bands of frequencies from escaping the core; thus confining a light beam within the photonic crystal fiber core. Additional polarization maintaining features may also be added to photonic crystal fibers in a similar way to polarization maintaining fibers in which rods of a different material or additional holes could be added along one axis to create two channels with different effective refractive indices. The shifted wavelength $\Delta\lambda$ in polarization maintaining fiber based fiber Bragg grating is obtained using $$\Delta\lambda = 2B\Lambda \quad (2)$$

where B is the stress-induced birefringence, and $\Lambda$ is the period in the fiber Bragg grating. The birefringence is related to differential stress by:

$$B = (C_1 - C_2)(\sigma_x - \sigma_y) \quad (3)$$

where $C_1$ and $C_2$ are the stress-optic coefficients of the fiber material which are silica in photonics crystal fibers. The values of $C_1$ and $C_2$ are $-6.9 \times 10^{-13}$ and $-41.9 \times 10^{-13}$ m$^2$N$^{-1}$ respectively [Y. Yang et al., "An embedded pressure sensor based on polarization maintaining photonic crystal fiber," Measurement Science and Technology 24, 094004 (2013)]. $\sigma_x$, $\sigma_y$ are the induced stresses in the orthogonal directions. FBGs integrated into photonic crystal fibers demonstrate enhanced sensitivity for strain sensing compared to conventional single mode fiber Bragg grating [H. V. Thakur et al., "Polarization maintaining photonic crystal fiber sensor embedded in carbon composite for structural health monitoring," Measurement 44, 847 (2011)]. Moreover, these fibers are typically made of pure silica which makes them relatively insensitive to temperature which may be useful in mock operations where temperature changes are not the primary metric to be measured. The wavelength shift in these fibers is also very linearly with applied pressure and temperature. FIG. 14 (c) shows an example of wavelength shifts versus transversal applied pressure and temperature from [Y. Yang et al., "An embedded pressure sensor based on polarization maintaining photonic crystal fiber," Measurement Science and Technology 24, 094004 (2013)]. Previously described multiplexing techniques could also be used with photonic crystal fiber based fiber Bragg grating.

Combination of Strain Detection Feedback Systems

In addition to the embodiments of strain detection feedback systems described above any combination of strain detection feedback systems may be employed to improve the effective capability of any individual systems. Two examples of such embodiments are provided in FIGS. 15 (a) and (b). The first block diagram FIG. 15 (a) shows an FBG based strain detection feedback system employing wavelength division and time division multiplexing. This system functions in the same manner as a time division multiplexed system where in addition to interrogating the reflected input signal for which time range it falls within it is also interrogated for what wavelength band it falls within (this may require the use of an external computer or microcontroller). The wavelength of this reflected input signal will be the altered Bragg wavelength of the FBG sensor. The detector may then analyze this reflected input signal to determine its wavelength (or range of wavelengths). Following this determination the time range may be used to assign the reflected input signal to a specific FBG sensor group (FBG: Xa, FBG: Xb, FBG: Xc). Following determination of the sensor group the specific sensor in the group (i.e. FBG: 1y . . . FBG: 6y) may be determined by the wavelength band the reflected input signal falls in. Once assigned a specific FBG sensor (FBG: 1a . . . FBG: 6c) the following equation may be used to determine a strain value corresponding to the reflected input signal.

$$\varepsilon = \frac{\lambda_{BS} - \lambda_{BO}}{\lambda_{BO}(1 - P_e)} - \frac{(\alpha_\Lambda - \alpha_\eta)\Delta T}{(1 - P_e)}$$

Where $\lambda_{BO}$ is the original Bragg wavelength of the assigned FBG sensor, $\lambda_{BS}$ is the wavelength of the reflected input signal and $\Delta T$ is the change in temperature at the FBG. The assigned FBG sensor along with this calculation then provides information as per the amount of applied strain and the location of that applied strain (i.e. a specific sensor 704).

Figure 15:
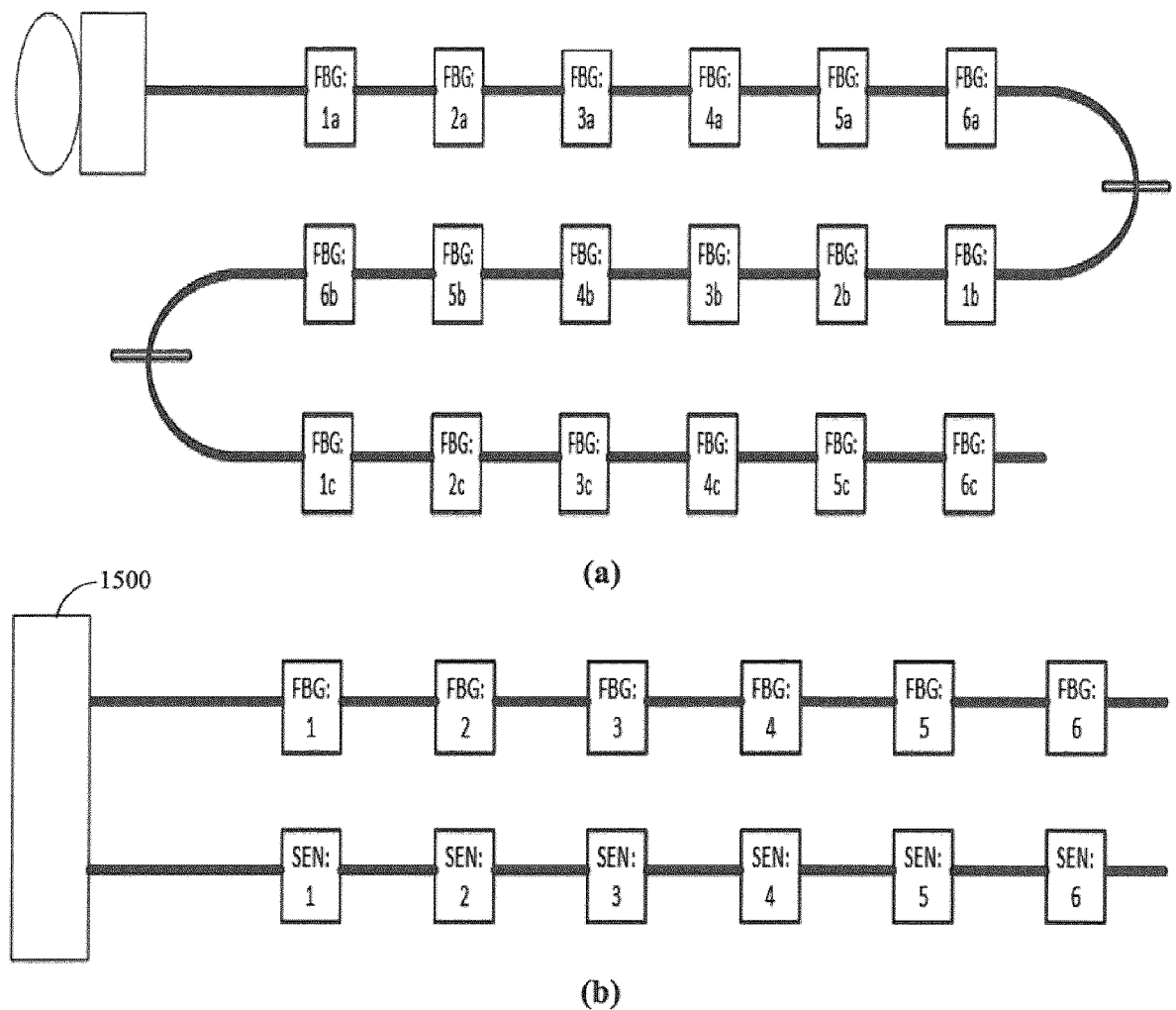
FIG. 15 (a) is an illustration of a combined multiplexing systems of fiber Bragg grating sensors.

The second block diagram FIG. 15 (b) shows a combination of an electrical, wavelength, and spatial division multiplexed strain detection feedback systems. To further clarify the block diagram shows an FBG based wavelength division multiplexed system spatially multiplexed with an electrical based strain detection feedback system. These individual systems work with the same principles used above where the spatial division multiplexing is used to combine the two other strain detection feedback systems with a single detector (which may be formed of multiple microcontrollers or computers). This system is simply an aggregation of parts with a common detector 1500 used to spatially multiplex the parts as opposed to the embodiment shown in FIG. 15 (a) which is a composition of systems. Regardless of this differentiation either combination may be used to improve the functioning of such strain detection feedback systems.

It should be noted that any of the sensors 604 of the strain detection feedback systems as described may also be implemented with wireless communication channels (i.e. communication channel 602 may be wireless) where possible as opposed to the non-wireless communication channels as described.

Shape Sensing Detectors Aligned Anatomically in a Spinal Phantom

In addition to the brain tissue phantom embodiment described above another embodiment of the tissue phantom device as disclosed herein would be a spinal tissue phantom as shown generally at 1680 in FIG. 16. In this embodiment 1680, the artificial ligaments, nerves, and intervertebral discs may be formed in entirety or in part of feedback system(s) monitoring particular metrics of the artificial tissue being replicated.

When integrating feedback systems in the tissue phantom device 1680 as disclosed herein in some embodiments it may be advantageous to use the physical hardware (i.e. parts) of the feedback systems to mimic actual anatomies contained within or on the specific anatomy being replicated by the tissue phantom device. This mimicry may take the form of anatomical properties, anatomical shapes, anatomical locations, and etc that will be described further as follows.

Referring to FIG. 16 in the embodiment 1680 the artificial Supraspinous Ligament 1610 may be formed of a fiber optic channel with cladding having a similar elastic module to that of the ligament to mimic its properties. This fiber optic channel may also be located in a position corresponding to where this Supraspinous Ligament 1610 is located in an actual patient anatomy to mimic its anatomical location. In addition the fiber optic channel may be formed of multiple channels each chosen to have a radius similar to that of the muscle fibers that form this Supraspinous Ligament 1610 to closely mimic the shape of it. Thus when a mock medical procedure is performed on the spinal tissue phantom this artificial Supraspinous Ligament 1610 will respond in a similar way to an actual Supraspinous Ligament 1610 and because it is formed of a fiber optic channel it may also simultaneously provide feedback metrics.

The fiber optic hardware used to form the Supraspinous Ligament 1610 in this embodiment may be integrated with any of the feedback systems as described herein which employ a fiber optic channel. Some example feedback systems may be the FBG, ODTR, or ODFR (below) feedback systems employing fiber optic channels as described herein, or any other feedback systems described herein or applicable for use with the fiber optic cable. It should be noted that when using the feedback system hardware to mimic the actual anatomy being replicated that the anatomical properties, anatomical shape, or the anatomical location may be mimicked individually or in any combination thereof. In addition these anatomical characteristics that may be mimicked are provided as examples only and should not be taken as limiting other possible anatomical characteristics which may be mimicked.

Also when integrating feedback systems in the tissue phantom device 1680 as disclosed herein in some embodiments it may be advantageous to map specific sensor characteristics to specific anatomical volumes of interest. For example when employing intensity division multiplexing in combination with spatial division multiplexing it may be advantageous to segregate the fiber optic channels being multiplexed by wavelength such that each wavelength may correspond to a different anatomical part of the tissue phantom device as disclosed herein. This is shown in the spinal tissue phantom device embodiment in FIG. 16 where each type of anatomical part formed with the spatially multiplexed fiber optic channels as described are differentiated from the other anatomical parts based on their input signal wavelength.

In FIG. 16 the Supraspinous Ligament 1610 is identified with an input signal wavelength range corresponding to a first color, the Inter-Spinal Ligament 1620 is identified with an input signal wavelength range corresponding to a second color, the spinal nerve 1640 is identified with an input signal non-visible wavelength, the annulus of the intervertebral discs 1630 are identified with an input signal wavelength range corresponding to a third color, and the Posterior Longitudinal Ligament 1600 is identified with an input signal wavelength range corresponding to a fourth color.

In some embodiments it may also be advantageous to register the locations of the feedback systems hardware (such as sensors) with the tissue phantom device as disclosed herein so as to know exactly where the feedback is originating from. For example in an embodiment where the feedback system hardware is chosen to mimic major fiber tracts in the brain phantom shown in FIG. 27 such as the optical tract 2700 it is advantageous to know where these major nerve bundles are such that a surgeon may avoid them similar to when they perform an actual surgery. Thus when performing a mock procedure such as a tumor resection if these areas are affected (as per the metric provided by the feedback system) the training surgeon may alter their trajectory for the real surgery they are preparing for. In an alternate embodiment the Supraspinous Ligament 1610 and Posterior Longitudinal Ligament 1600 shown in FIG. 17 may be initially placed in a known orientation and provided to the surgeon. These two ligaments may then be produced with an integrated shape sensing feedback system that may provide feedback to a user of the spinal tissue phantom during a mock procedure as to the shape of the spine. This type of shape sensing feedback system may be advantageous for use in some embodiments of the tissue phantom as disclosed herein as it provides dynamic movement information about the mock anatomy during the mock medical procedure.

Figure 17:
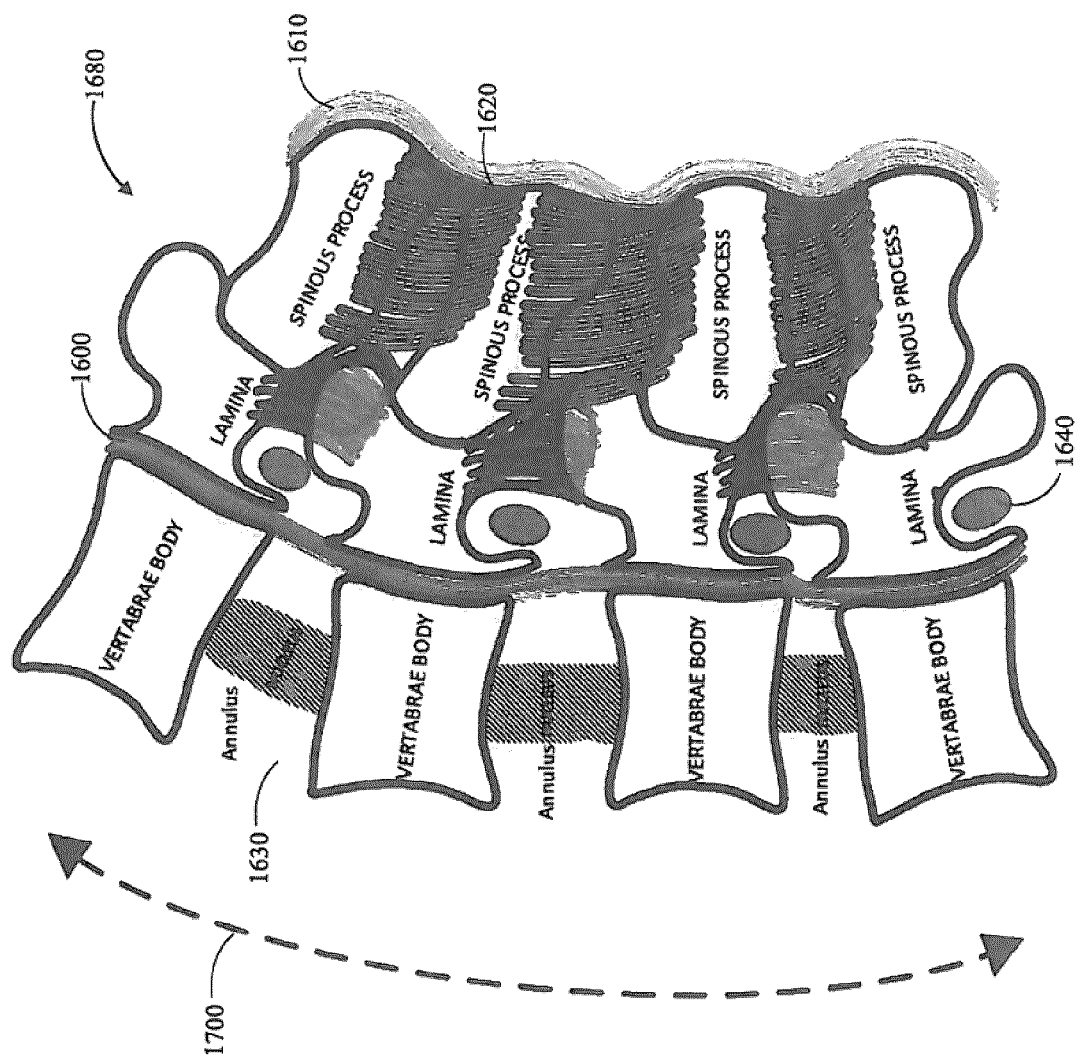
FIG. 17 is an illustration of a curving spinal phantom with intergrated feedback systems.

It is a common occurrence in spinal surgery for the vertebrae of the patient to move relative to one another during a surgical procedure as they are shaped to naturally do so such as shown by arrow 1700 in FIG. 17. Thus knowing the initial orientation of the spinal tissue phantom 1680 and being able to track its shape using a shape sensing feedback system will allow for the replication of such an occurrence in a mock procedure to occur and also allow for the training surgeon to dynamically track the positioning and shape of the spine during said mock procedure. This may assist training surgeons improve their skill and account for unexpected conditions during actual spinal surgeries. An example of such feedback systems would be a shape sensing detection feedback system that may be used to monitor the movement of the vertebrae relative to one another during a mock medical procedure. The shape sensing sensors may take the form of optical fiber cables or a suitable tissue like material embedded with or incased within an organic flexible strain gauge array which will be described in further detail below in the descriptions of FIGS. 18 (i) and (ii).

Figure 18:
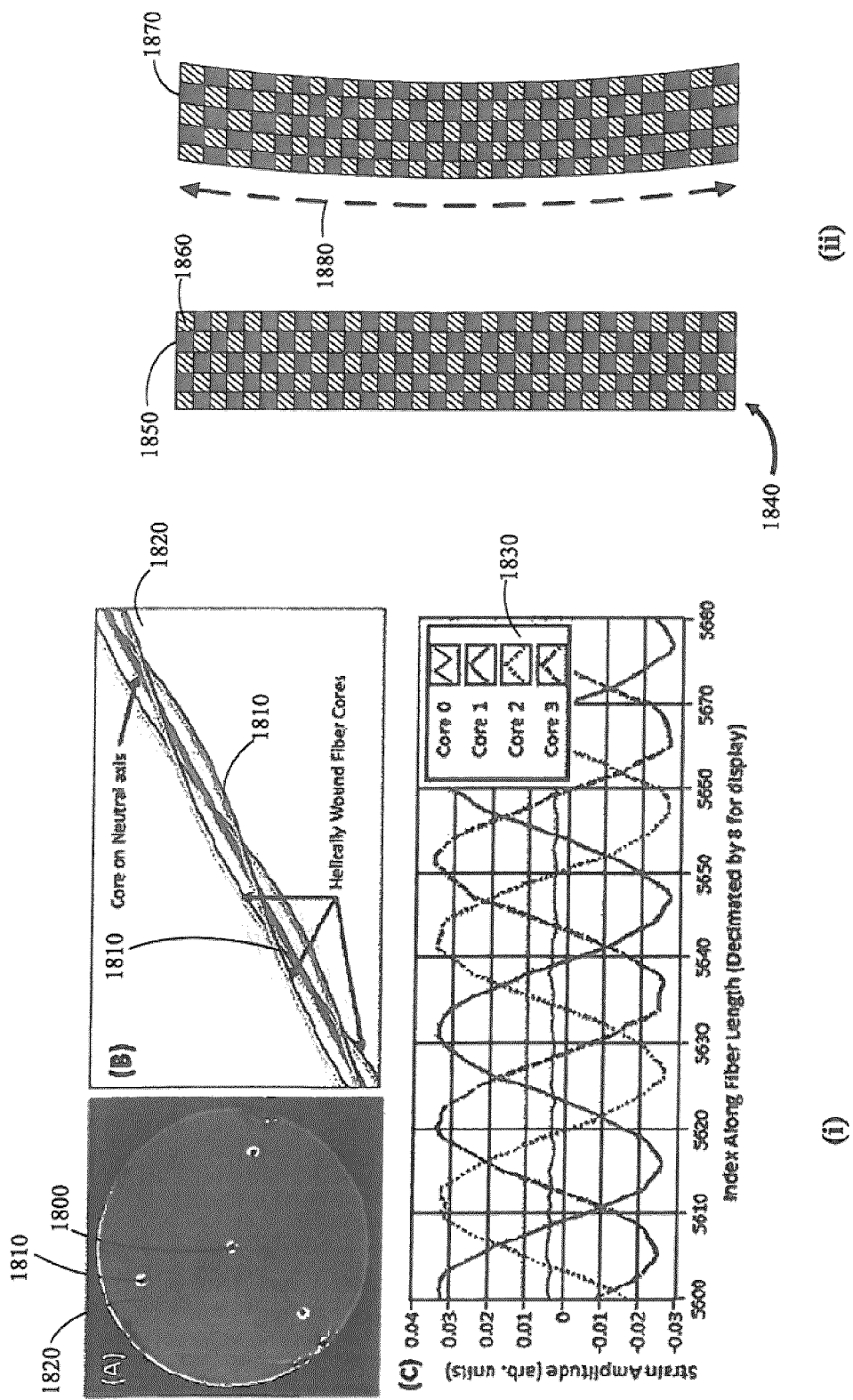
FIG. 18 (i) is an illustration of a shape sensing cable.

FIG. 18 (i) shows a diagram depicting a shape sensing fiber optic cable 1820. The cable contains a central fiber optic channel 1800 surrounded radially by three additional fiber optic channels 1810 each extending in a helical configuration along the length of the cable 1820 and aligned 120° apart from one another. Optical Frequency Domain Reflectometry (OFDR) is used to interrogate each fiber optic channel and determine the distributed strain amplitude of each fiber optic along the length of the cable 1820. When the cable is deformed in a curve configuration the radial cores undergo alternating states of tension and compression through the region of the curve. An example of a strain response 1830 of this cable on an interval having a typical curvature is shown in FIG. 18 (a). The magnitudes and phases of these strain responses along with knowledge of their relative location to one another at a specific distance in the cable may then be used to infer the magnitude and direction of curvature of the shape sensing cable. A further clarification may be found in the paper [Luna Innovations Inc.; Fiber Optic Shape Sensing, Current State of Technology: Publisher, Jun. 21, 2013].

FIG. 18 (ii) shows a diagram depicting a shape sensing strain gauge array 1840. The strain gauges in this array work analogously to the strain gauges described above. The figure depicts individual strain gauges 1850 on a flexible substrate 1860. This flexible substrate 1860 works as a circuit board carrying signals to and from an interrogation circuit (such as contained within a microcontroller (not shown) for example) that may infer the shape of the entire body of the array based on the strain readings of individual sensors. This can be accomplished by mapping the individual strain gauges to a virtual model of the shape sensing strain gauge array or other applicable means. In order to infer the shape of the array the signals may be encoded depending on the location of the sensor. As the strain gauge shape sensing device is flexed 1880 the individual sensors 1850 are strained accordingly such as sensor 1870 on the right hand side of FIG. 18 (ii).

Alternative Surgical Metrics

Figure 19:
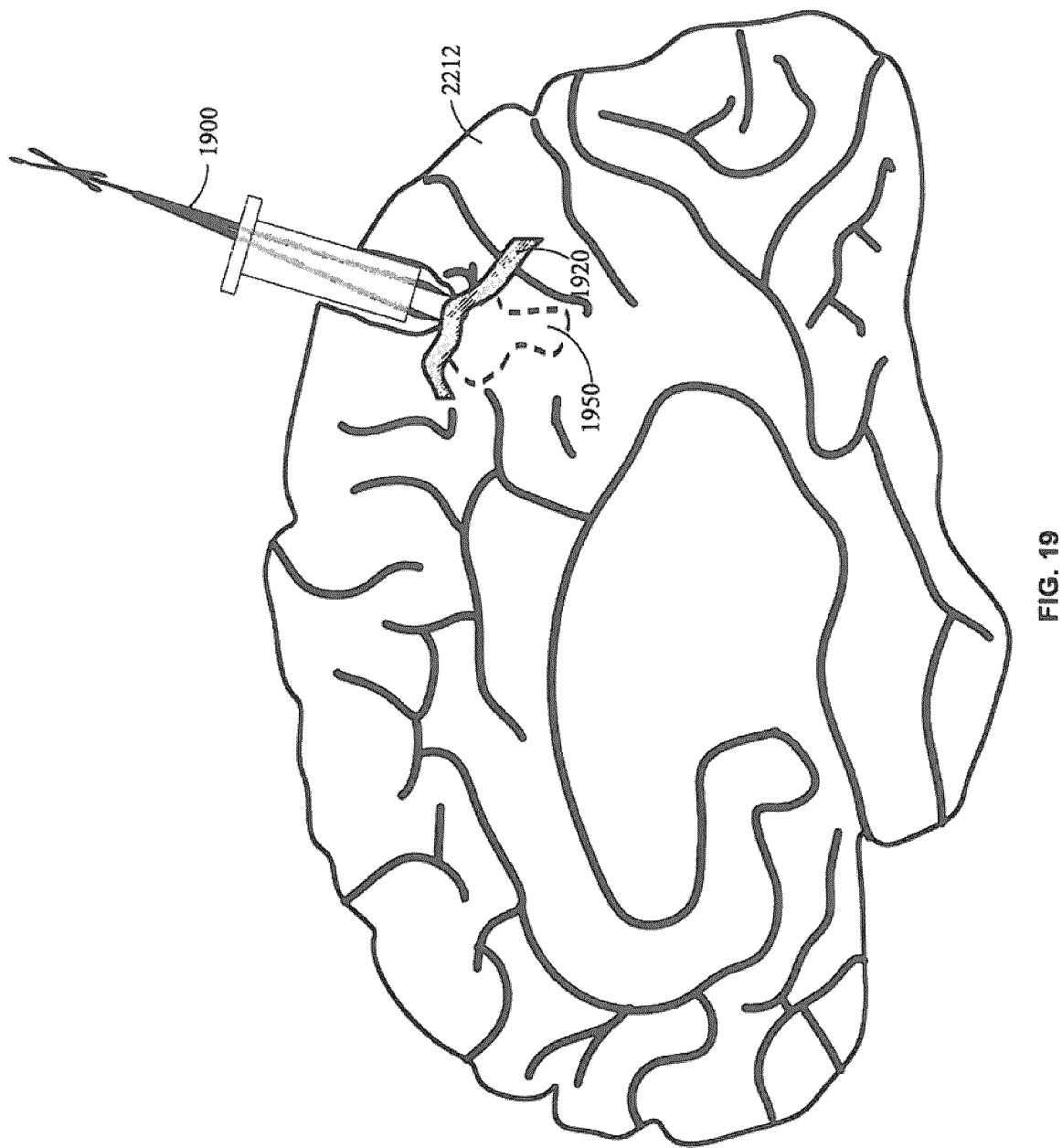
FIG. 19 is an illustration of a mock port based resection surgery on a brain phantom.
Figure 20:
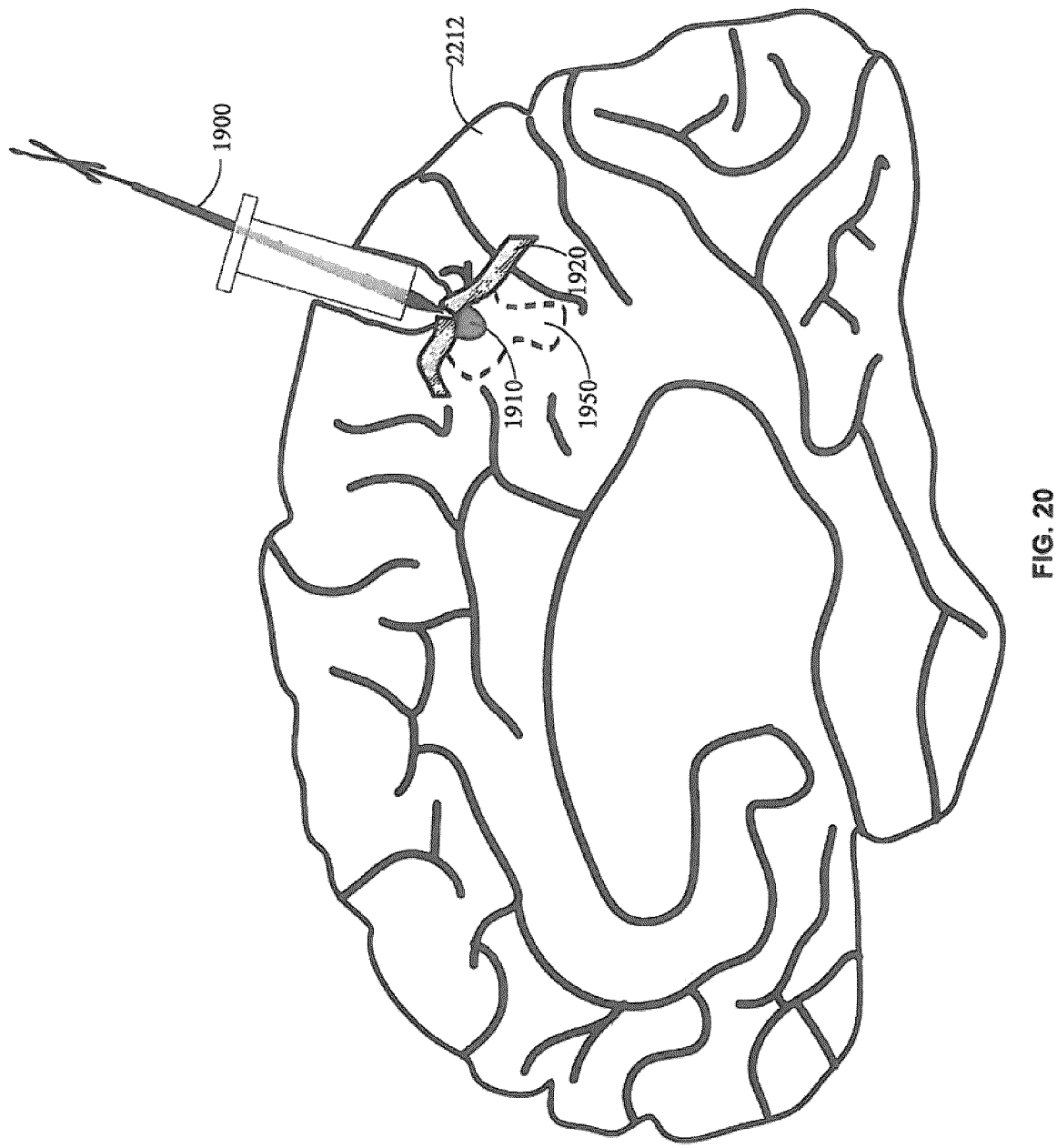
FIG. 20 is an illustration of a progressing mock port based resection surgery on a brain phantom.

During mock surgical interventions with tissue phantoms alternative feedback metrics in addition to the strain measurements as described in detail above may also be significant in providing information as to the relative success or progression of a mock surgical operation. Referring to FIGS. 19 and 20 for example during port based medical procedures bipolar forceps 1900 are commonly used to cauterize bleeding vessels 1920 yet the thermal damage 2000 (best seen in FIG. 20) caused by this tool 1900 is hard to determine at times and may never be determined during an actual surgery. In yet another example functional stimulation is commonly performed in or on the surface of the brain, and when conducted on the surface, any thermal damage may or may not be visible, but when conducted in the depth of the brain where only a probe can gain access, the damage will not be apparent until either the patient consciously notices a difference in their ability to function or the damage is imaged.

There are also medical procedures that attempt to damage unwanted tissue and remove it. For example a method of removing tissue involves radiation therapy wherein high doses of radiation are applied to an area containing a tumor in order to damage the desired tissue so the body may autonomously remove it.

These feedback metrics although difficult to determine during an actual medical procedure may be rendered determinable in a mock procedure given the tissue phantom device as disclosed herein is employed. Thus such metrics may improve a training surgeon's ability to better predict the limits of their intervention in order to produce desirable results. Without such a training tool it may be otherwise difficult to estimate without extensive practical experience causing trauma to actual patient's livelihoods.

One way to produce such a feedback metric would be to create a tissue phantom of a matrix in its entirety or at least partially such that it has inherent characteristics that would cause the matrix properties to change as a result of exposure to the applicable interventional therapies such as heat from an electrocautery tool, electrical current from a functional stimulation tool, or radiation from a radiation therapy tool (such as, but not limited to, a gamma knife). Tissue materials that may exhibit these properties will be described further below.

Thermally/Optically Reactive Material

In an embodiment, for example the tissue phantom device 2212 shown as part of the tumor resection procedure depicted in FIGS. 19 and 20, a thermally activated crosslinker may be suspended in the targeted volume 1950 (or the entire volume 2212) of the tissue phantom device 2212. This thermally activated crosslinker when exposed to an increased temperature, for example at the cauterization end of the electrocautery tool 1900 could activate a crosslinking reaction between polymer chains causing an increased rigidity at the targeted volume, shown as the sub-sectional volume 2000 of the targeted volume 1950 in FIGS. 20 (*a*) and 20 (*b*).

Once the mock procedure has been completed a comparison of the denser volume with the planned mock volume which was to be operated on may be done to provide a feedback metric to the training surgeon as to the level of success of the performed mock procedure. The denser volume may be acquired through processes such as but not limited to, dissecting the tissue phantom device and removing the denser area, imaging the tissue phantom device, or performing a biopsy on the device.

Furthermore in an alternate embodiment of the tissue phantom device 2212 shown as part of the mock tumor resection procedure depicted in FIGS. 19 and 20, may be produced of a hydrogel material. If then a heated electrocautery instrument 1900 was applied near the area 1950 by a training surgeon the hydrogel in the region 2000 may cause a change in water content (due to evaporation) and consequently the density in the region 2000. This would result in a measurable feedback metric analogous to that provided by the crosslinker material mentioned above.

In an example, using a hydrogel based material, the change in water content of the hydrogel as a response to the heat emanated by a cauterization could modulate the density of the hydrogel in the targeted zone, causing a measurable effect.

In a second embodiment, a solid material with a melting range commensurate with the temperature reached by the applicable probe such as the electrocautery tool 1900 shown in the tumor resection procedure in FIGS. 19 and 20 may be incorporated into the target volume 1950 or as shown in the figure the entire volume of the tissue phantom 2212. On melting during a treatment, loss of this material and the extent of the resulting rheological change could be used as a feedback metric for the level of success of the mock procedure. Again once a mock procedure has been completed the amount of matrix that had been melted may be used as an indicator of success of the surgery. And again the melted volume may be determined through processes such as but not limited to, dissecting the tissue phantom device and removing the denser area, imaging the tissue phantom device, or performing a biopsy on the device.

In an alternate embodiment an electrochromic material may be used in place of the material with a melting point commensurate with the temperature reached by the applicable electrocautery tool during a cauterization of a tissue. The electrochromic material would change color (temporarily or permanently) depending on the voltage applied thus providing a feedback metric to the training surgeon using the tissue phantom device as disclosed herein. Using a reversible electrochromic material may be advantageous for use in the mock tumor resection procedure mentioned a priori as the damage caused by the electrocautery device would be seen immediately by the training surgeon which would allow them to change their use of the device throughout the remaining surgery to cause less damage.

In an alternate embodiment employing a reversible electrochromic material it might be advantageous to form the tissue phantom of a translucent material surrounding the target volume (such as 1950 as mentioned above). This target volume would contain the suspended electrochromic material. The translucency of the tissue phantom would facilitate the change in chromaticity of the material to be more easily observed by the training surgeon. This may also potentially allow the tissue phantom to be preserved in scenarios where the phantom would otherwise be dissected.

Some non-limiting examples of electochromic materials may be some of the transition metals as mentioned in the paper [Somani, Prakash R., and S. Radhakrishnan. "Electrochromic materials and devices: present and future." *Materials Chemistry and Physics* 77.1 (2003): 117-133.]

Tool Integrated Phantoms

Feedback metrics such as those mentioned above are helpful for improving a training surgeon's ability in reducing damage to unwanted regions of a tissue phantom however there are also advantages in having detection metrics which are directly dependent on the training surgeons (or other users) interventional movements with their tool. For example during cortical mapping of the brain it is common for a surgeon to use a stimulation probe such 2100 shown in FIG. 21 to stimulate particular white matter tracts to confirm there function and location. When performing tumor resection surgeries it is common for a surgeon to plan to avoid particular tract bundles to minimize trauma to the patient. In another example when faced with vasculature in or around a volume of unhealthy tissue in the brain to be removed, it is common for a surgeon to strip the vasculature with a suction tool, if it is an important artery or vain. In yet another example during deep brain stimulation (DBS) procedures surgeons commonly employ a microelectrode recording tool to confirm the DBS probe has reached the target location (in most cases the STN) by listening to the induced current in the probe. There are many embodiments which may be employed in the tissue phantom device as disclosed herein as will be further discussed as follows.

To better facilitate a mock cortical mapping exercise for a training surgeon, an embodiment of a mock tissue phantom device as disclosed herein may be produced with artificial functional tracts that may provide metrics reflective of functional stimulation responses. An exemplary embodiment of such a tissue phantom device is provided in FIG. 21. The left side of the figure depicts the sulci of the brain 2102 (through the mock craniotomy 2106 and mock skull 2104) and a stimulation probe 2100 inserted through one of the sulci 2102 into the brain phantom 2112. The right side of the figure shows the internal structures contained within the brain phantom matrix material. These internal structures 2108 replicate the tractography of the brain. Based on interaction with the functional stimulation probe 2100 the artificial brain tracts 2108 may provide information reflective of a functional stimulation response of a real fiber tract of a brain.

The artificial brain tracts shown in FIG. 21 are conductive cables wherein each separate segment of tractography 2108 is a separate conducting cable. The conducting cables are connected to a central cable 2110 that runs them to the ground of the voltage source 2114. The stimulation probe 2100 in FIG. 21 is connected to the positive end of the voltage source. A computer 2116 is connected to the voltage source 2114 which may determine which artificial tracts cable 2108 is stimulated if the stimulation probe makes contact with one of the artificial tracts during a mock cortical mapping procedure. This can be accomplished simply by measuring the current running through each of the artificial tractography cables 2108.

It should be noted that there is enough inherent resistance along any of the artificial tractography cables 2108 to allow for an electrical current to flow through them. The computer 2116 may then provide information as to which tract has been contacted by the stimulation probe. The exemplary embodiment of a mock tissue phantom as shown in FIG. 21 thus allows for a surgeon to perform a mock cortical mapping exercise with additional knowledge of what tracts they may be stimulating. This may improve a training surgeon's ability to accurately reach the target tractography in a patient's brain during an actual procedure, especially if the artificial tractography 2108 and brain phantom surface mimic the tractography and surface of an actual patient's brain.

Figure 22:
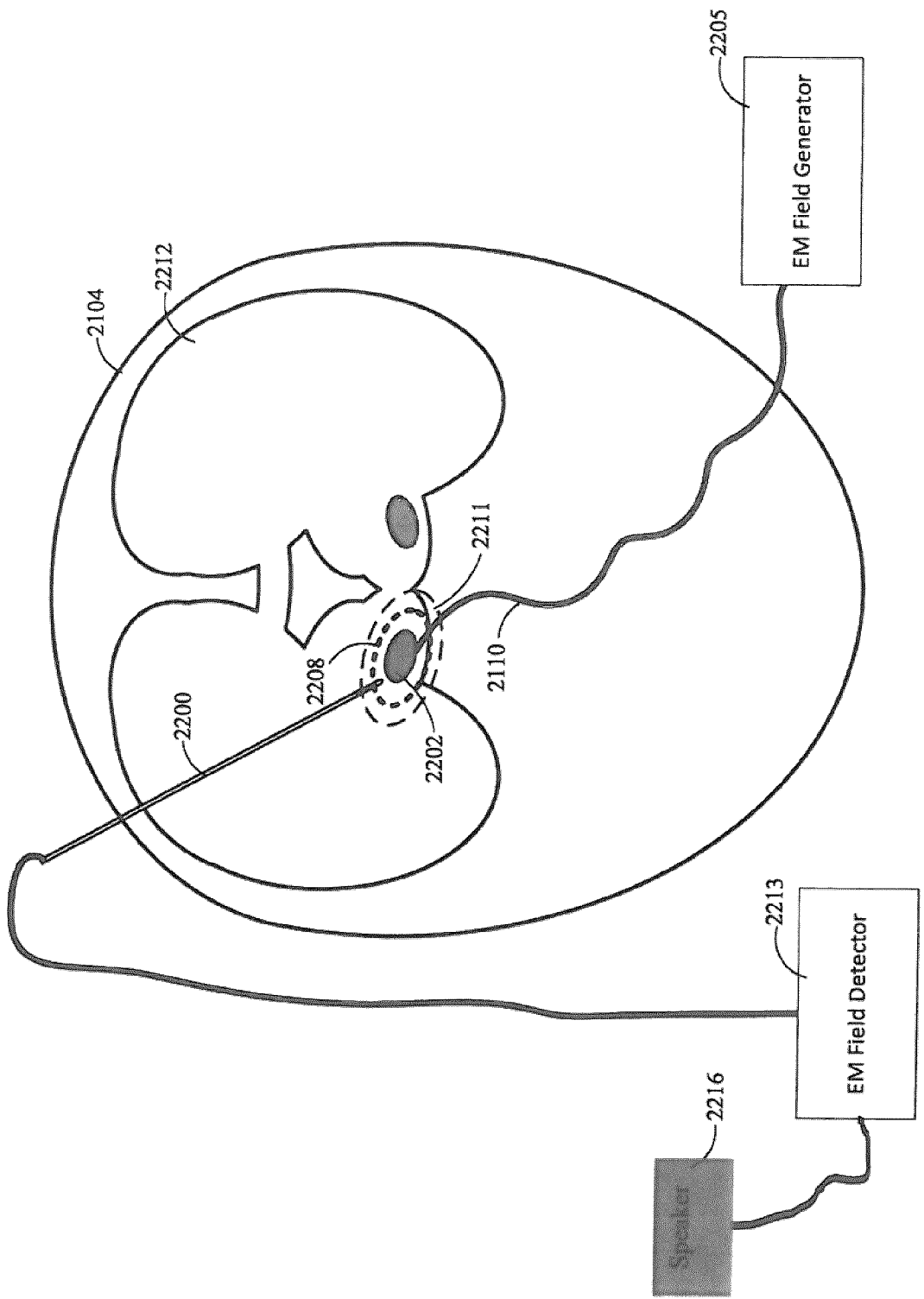
FIG. 22 is an illustration of a brain phantom with built in EM feedback system for a mock deep brain stimulation (DBS) procedure.
Figure 23:
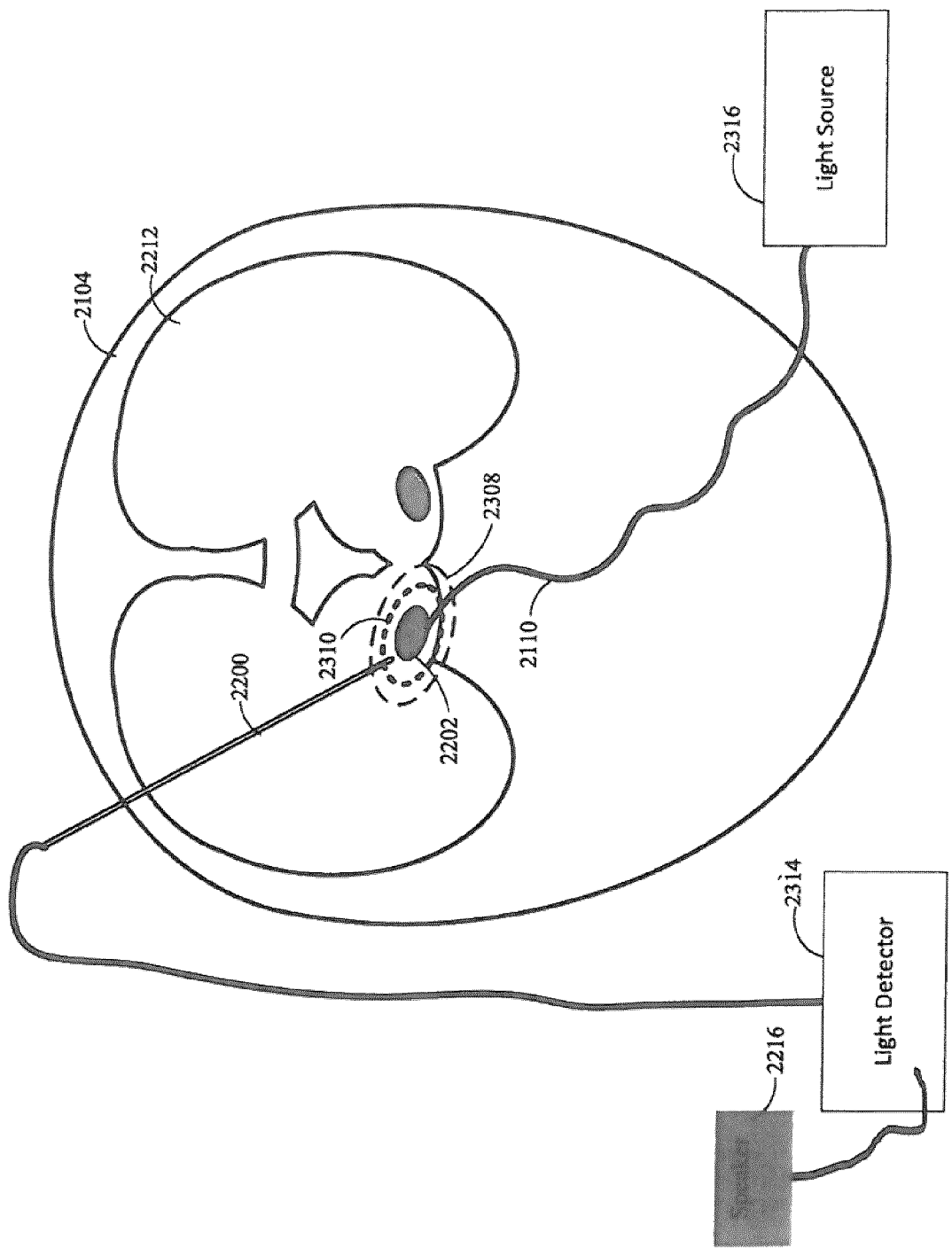
FIG. 23 is an illustration of a brain phantom with built in optical feedback system for a mock DBS procedure.

To better facilitate a mock DBS procedure exercise for a training surgeon, an embodiment of a mock tissue phantom device as disclosed herein may be produced with an artificial STN (Sub thalamic Nucleus) that may provide metrics reflective an STN response. Two exemplary embodiments of such a tissue phantom device are shown in FIGS. 22 and 23. Common to both embodiments is a mock skull 2104 and internal brain phantom 2212 through which a (mock or actual) MER (Microelectrode recording) device 2200 is being advanced along a trajectory towards a target, in this case the mock STN 2202. In the first embodiment shown in FIG. 22 an EM field generating module 2205 is connected through a cable to the center of the mock STN where an EM field generator transmitter probe (such as a battery powered solenoid) is then used to induce an EM field similar to that produced by an STN when implanting a DBS probe during actual DBS procedures. As is a common occurrence in the field the STNs EM field may be stronger in a closer vicinity to the STN such as that shown by the dashed line boundary 2208 and weaker further away such as on the boundary shown by dashed line boundary 2211.

The MER device 2200 in this case may be an actual device to better replicate the DBS procedure. The MER device 2200 is connected to an EM field detector 2213 module and the device itself contains an EM field detector. This EM field detector module 2213 will then relay the detected EM field as an audible signal through a speaker 2216 that may be used by the training surgeon to determine where the tool 2200 is in the mock internal brain phantom 2212 (i.e. where the tool may be relative to the vicinity of the STN 2202).

The embodiment shown in FIG. 23 is analogous to the embodiment shown in FIG. 22 in that mock procedure may be performed in the same manner only that the EM field would be replaced by a photon intensity flux through a diffusing medium and the MER device would be in the form of an optical luminous intensity detector to detect the strength of the photon flux at various locations in the internal brain phantom 2212. In this embodiment the tissue phantom containing the mock STN is made of a translucent material that diffuses (scatters) photons as opposed to absorbing them. In this embodiment the STN 2202 is also constrained to be a photon diffusing material, for better replication of an actual DBS procedure it would be desirable to have the STN 2202 be transparent such that any incoming light would pass through it and only begin diffusing into the internal brain phantom material 2212 surrounding it. This would be closer to the EM field of an actual STN as it is for the most part consistent throughout the STN and only begins to reduce outside of it in the brain. The light source module 2316 in this embodiment is equivalent to the EM field generator module 2205 in the embodiment shown in FIG. 22. Similarly it is routed to the mock STN 2202 through a channel (fiber optic in this case) and is emitted in the STN where it will create a photon flux field around the STN 2202 and a strong substantially consistent photon flux field within the STN 2202.

As is a common occurrence in the field, the STNs equivalent photon flux field may be stronger in a closer vicinity to the STN such as that shown by the boundary 2310 and weaker further away such as on the boundary shown by 2308. In this embodiment the MER device 2200 is connected to an optical detector module 2314 and the device itself contains a light pipe to transfer photons to the optical detector module 2314 to be detected. This optical detector module 2314 will then relay the detected photon intensity as an audible signal through a speaker 2216 that may be used by the training surgeon to determine where the tip of device 2200 is in the mock internal brain phantom 2212 (i.e. where the tip of device 2200 may be relative to the vicinity of the STN 2202).

To better facilitate a mock tumor resection exercise for a training surgeon, an embodiment of a tissue phantom device as disclosed herein may be produced with artificial functional tracts that may provide metrics reflective of tractography damage. An exemplary embodiment of such a tissue phantom device is provided in FIGS. 24 to 27. These figures show the progression of a commonly performed port based tumor (not shown) resection with two simultaneous views of the internal structures and external form of the tissue phantom. FIGS. 24 (a) and 24 (b) shows the mock surgery before an access port 100 is inserted into a sulcus 2400 of the mock brain 2212, FIGS. 25 (a) and 25 (b) show the access port during cannulation to the bottom of the sulcus 2400, and FIGS. 26 (a) and 26 (b) show the access port 100 after it has penetrated the bottom of the sulcus 2400 as it is being advanced to the target.

In an embodiment the artificial tracts 2410 (FIG. 24 (b)) may be in the form of fiber optic channels wherein a light source (not shown) may inject light of any wavelengths into the channels. If one of the fiber optic channels representative of an actual brain tract is then broken, such as fiber 2600 in FIG. 26 (b), it would release light indicating the artificial tract had been damaged. In order to allow the released light to be observed outside the artificial brain 2212 material it would be advantageous for the artificial brain 2212 to have a translucent characteristic such that the released light may diffuse into the material and be seen by the training surgeon practicing the exercise. Another manner in which the released light may be communicated to the surgeon would be through the use of a photochromic material such as that described in the embodiment above. In an embodiment specific groups of tracts may be injected with specific wavelengths of light indicative of the tract type as shown in FIG. 27. For example the tracts 2410 shown radiating out from the central tract 2420 correspond to the Corona Radiata and may be chosen to be represented by light with a specific wavelength range potentially corresponding to a specific color such as yellow.

In another example the optical tract may be chosen to be represented by light with a specific wavelength range potentially corresponding to a specific color such as blue. In an alternate embodiment the fiber optic channels may be representative of vasculature in the brain. This may be advantageous in that a surgeon training to strip vasculature in a volume of unhealthy tissue would be informed if they damaged the artificial vasculature and caused a bleed to occur. To implement this the wires of strain detecting feedback system shown in FIG. 7 (c) and described above may be used as the vasculature. In an embodiment this artificial vasculature would ideally have the same material properties as actual vasculature. For example, toughness, modulus of elasticity, hardness, etc. similar to the fiber optic channel used to form the Supraspinous Ligament as described above.

Figure 25:
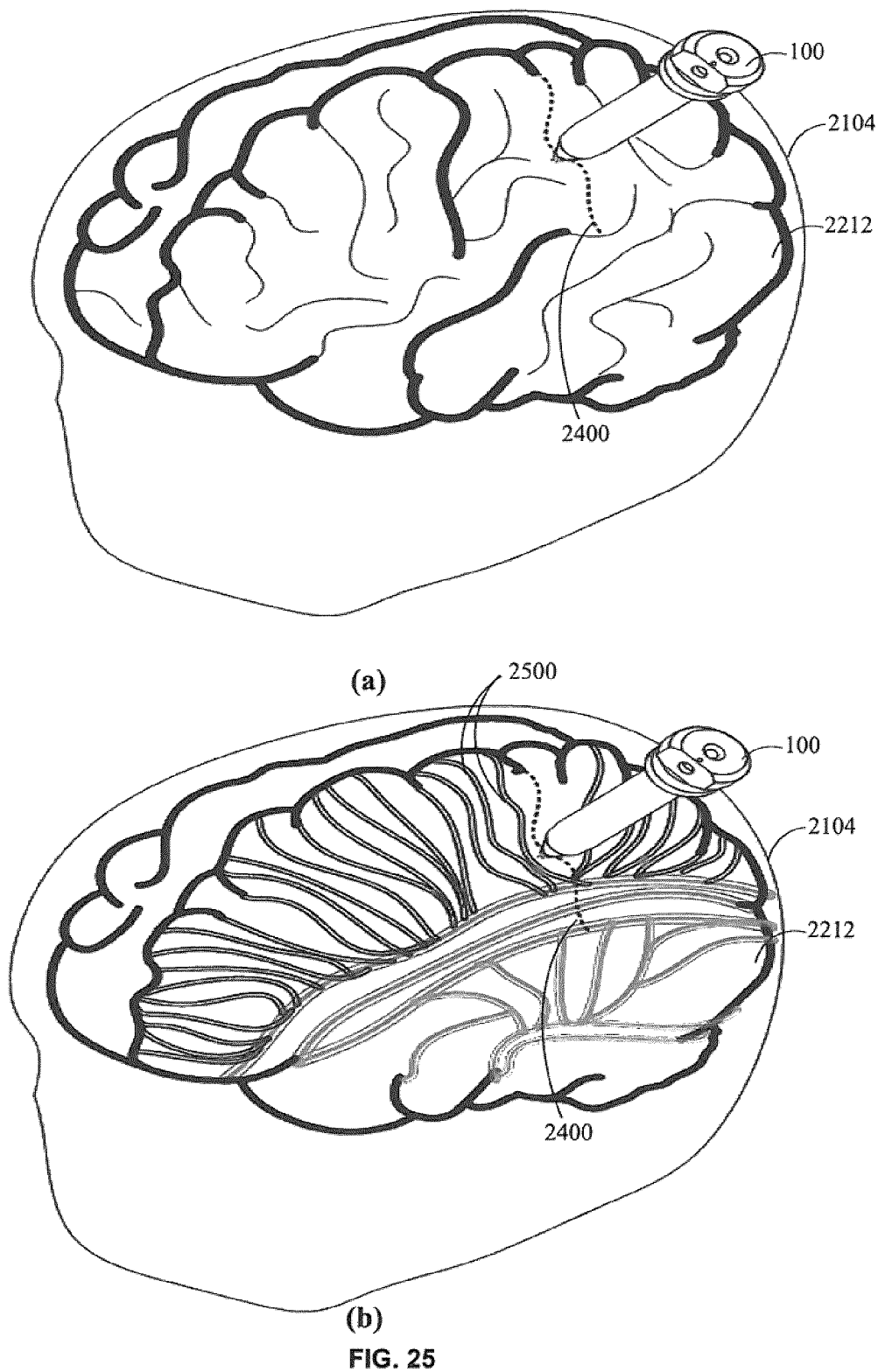
FIGS. 25 (a) and (b) are similar to FIGS. 24 (a) and (b) but shows the access port during cannulation to the bottom of the sulcus.
Figure 26:
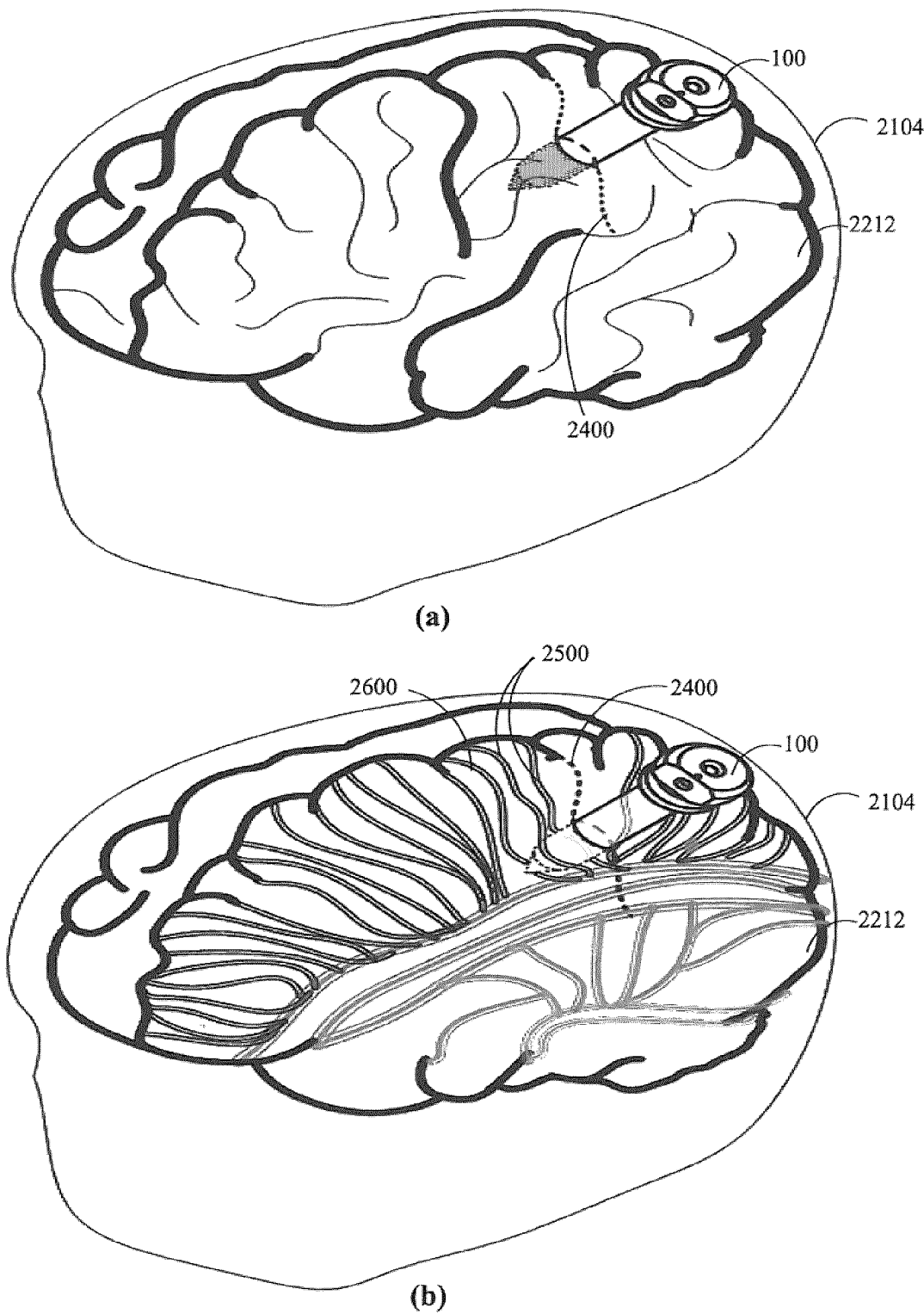
FIGS. 26 (a) and (b) are similar to FIGS. 25 (a) and (b) but depicts the sulci of the brain and the access port after it has penetrated the bottom of the sulcus as it is being advanced to the target.
Figure 27:
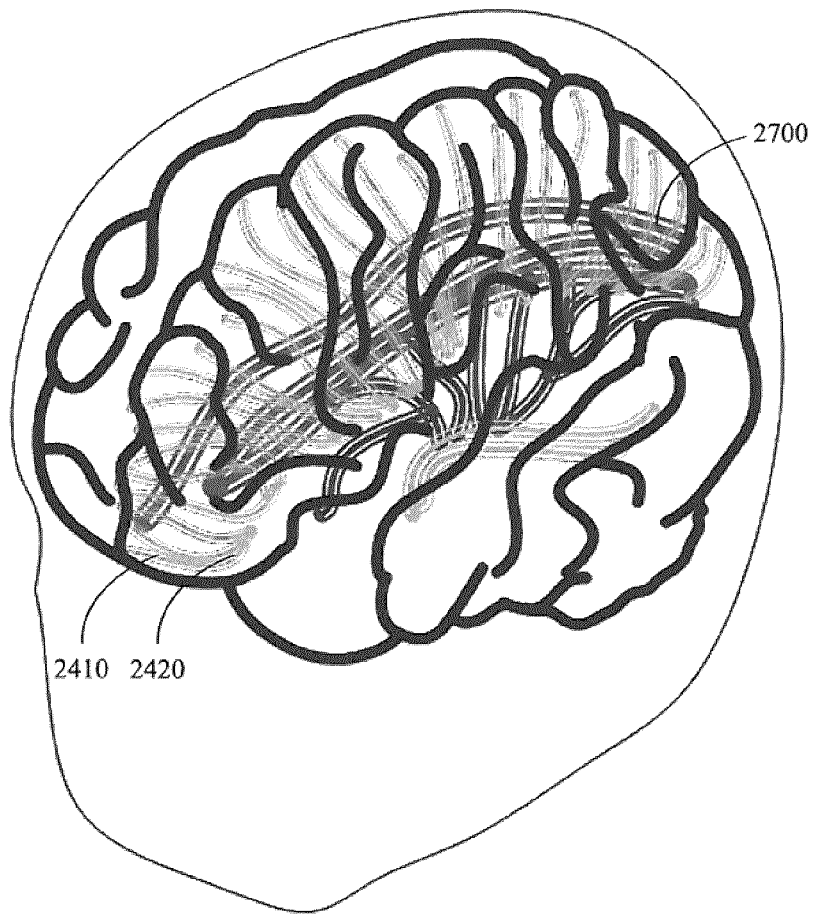
FIG. 27 is an illustration of a brain phantom with an integrated feedback system network with anatomical correlation to its detection properties.

In an alternate embodiment of the tissue phantom device shown in FIGS. 24 to 26 the strain detection feedback system shown in FIG. 7 (c) may be employed where each of the electrical communication channels 734 may correspond to a tract 2410. Thus if any of the tracts are damaged the surgeon may be informed by the microcontroller. This embodiment may not require the artificial brain 2212 material to have any specific properties like the previous embodiment.

The sensorized phantoms disclosed herein may be generic phantoms used simply for training purposes. In addition, the phantoms may be patient specific phantoms, produced based on preoperative imaging of the anatomical part of the patient undergoing the medical procedure. Thus if a patient has a brain tumor, preoperative imaging of the patient's brain may be used to construct a lifelike brain phantom including the tumor, with the brain structures and tumor being made of material selected to mimic the biomechanical properties of the brain structures and tumor. This phantom will give the clinician an opportunity to practice the medical procedure in a very realistic manner.

It should be noted that it is advantageous to orient any strain sensors and artificial tracts or other artificial anatomical parts with built in sensors in a manner consonant with human anatomy. It is also advantageous to have these artificial anatomies designed with properties as similar to the actual anatomies being mimicked as possible.

It should be noted that any of the surgical exercises employing the tissue phantom device embodiments as disclosed herein should not construed as limiting the use of the tissue phantom device to just those exercises and are given as examples to assist in understanding the tissue phantom device only.

While the Applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. A sensorized tissue phantom for performing a mock surgical procedure, comprising: a tissue phantom mimicking an anatomical part, the tissue phantom comprising at least one sensorized portion configured to provide feedback metric when said at least one sensorized portion is interacted during a mock surgical procedure, said at least one sensorized portion comprising at least one sensor, the at least one sensor comprising a sensing material, the at least one sensing material mimicking tissue as a part of the tissue phantom, the at least one sensing material mimicking at least one of directionality, density, and elasticity of the tissue, and the sensing material comprising at least one electromagnetic radiation source and at least one of: at least one fluorophore, at least one photo-reactive material, at least one thermally-reactive material, at least one electrochromic material, and at least one radiochromic material, wherein the at least one electromagnetic radiation source is embedded in, and in close proximity to, a preselected portion of said tissue phantom corresponding to a preselected anatomical section of said anatomical part; and a detector configured to detect electromagnetic radiation signals emitted by the at least one electromagnetic radiation source.

2. The sensorized tissue phantom of claim 1, wherein said at least one sensorized portion represents at least one of: at least one anatomical location, at least one selected biomechanical property, at least one physical shape, and at least one anomalous physiological structure undergoing the mock surgical procedure of at least one portion in said anatomical part.

3. The sensorized tissue phantom of claim 1,
wherein the at least one sensor comprises a plurality of sensors disposed in said at least one sensorized portion,
wherein the plurality of sensors is distributed throughout said at least one sensorized portion,
wherein the plurality of sensors is coupled with a communication channel, and
wherein the detector is coupled with the plurality of sensors by way of said communication channel.

4. The sensorized tissue phantom of claim 3, further comprising a computer processor coupled with said detector, said computer processor programmed to visually display an output from each said at least one sensor of the plurality of sensors.

5. The sensorized tissue phantom of claim 4, further comprising an audio alarm device coupled with said computer processor.

6. The sensorized tissue phantom of claim 3,
wherein said communication channel comprises at least one optical fiber,
wherein said plurality of sensors comprises: a plurality of Fiber Bragg gratings spaced along said at least one optical fiber and a light source coupled with said at least one optical fiber, and
wherein said detector is configured to detect a spectral response from light reflected by said plurality of Fiber Bragg gratings.

7. The sensorized tissue phantom of claim 3,
wherein the communication channel comprises an optical fiber,
wherein the optical fiber is coupled with a light source,
wherein said detector comprises an optical time domain reflectometer, and
wherein said optical time domain reflectometer detects a reflected light signal trace.

8. The sensorized tissue phantom of claim 3,
wherein said communication channel comprises at least one electrical wire,
wherein each said at least one sensor of the plurality of sensors further comprises at least one electrical strain gauge, and
wherein said detector detects strain experienced by each said at least one sensor of the plurality of sensors.

9. The sensorized tissue phantom of claim 3,
wherein said communication channel comprises at least one electrical wire,
wherein each said at least one sensor of the plurality of sensors further comprises an organic semiconductor strain gauge, and
wherein said detector detects strain experienced by each said at least one sensor of the plurality of sensors.

10. The sensorized tissue phantom of claim 3, wherein, the sensing material comprises said at least one fluorophore which is embedded in the tissue phantom, and the at least one optical fiber operates as the communication channel, and wherein the at least one optical fiber is coupled with at least one light source, and the at least one light source configured to excite the at least one fluorophore embedded in the tissue phantom, such that, upon at least one condition of a breakage and a local bend, due to contact with a given optical fiber, light is emitted into the tissue phantom to excite the at least one fluorophore in close proximity to a location of said condition.

11. The sensorized tissue phantom of claim 1, wherein the at least one sensor of the plurality of sensors represents at least one of: an anatomical location, at least one selected biomechanical property, at least one physical shape, at least one anomalous physiological structure undergoing the mock surgical procedure of at least one portion in said anatomical part.

12. The sensorized tissue phantom of claim 1,
wherein said detector comprises a probe insertable into the preselected portion of said tissue phantom, and
wherein said detector is configured to detect electromagnetic radiation from said preselected portion of said tissue phantom.

13. The sensorized tissue phantom of claim 12,
wherein said detector is coupled with an audible speaker, and
wherein the audible speaker is configured to emit an audible signal when said detector detects electromagnetic radiation indicative of a location said preselected portion of said preselected portion of said tissue phantom.

14. The sensorized tissue phantom of claim 1, wherein the sensing material is sensitive to selected stimuli.

15. The sensorized tissue phantom of claim 14, wherein said sensing material represents at least one of: an anatomical location, at least one selected biomechanical property, at least one physical shape, at least one anomalous physiological structure undergoing the mock surgical procedure of at least one portion in said anatomical part.

16. The sensorized tissue phantom of claim 14, wherein said sensing material, sensitive to selected stimuli, comprises at least one of: an electrically sensitive material, a pressure sensitive material, an optically sensitive material, a thermally sensitive material, a radiation sensitive material, and a sound sensitive material.

* * * * *